(12) United States Patent
Miller

(10) Patent No.: US 8,167,818 B2
(45) Date of Patent: May 1, 2012

(54) BIOPSY APPARATUS WITH VACUUM RELIEF

(75) Inventor: Michael E. Miller, Trafalgar, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 12 days.

(21) Appl. No.: 12/359,857

(22) Filed: Jan. 26, 2009

(65) Prior Publication Data

US 2009/0137927 A1      May 28, 2009

Related U.S. Application Data

(60) Division of application No. 10/970,269, filed on Oct. 21, 2004, now Pat. No. 7,497,833, which is a continuation of application No. 10/639,569, filed on Aug. 12, 2003, which is a division of application No. 09/864,031, filed on May 23, 2001, now Pat. No. 6,638,235, said application No. 10/970,269 is a continuation of application No. 10/848,278, filed on May 18, 2004, which is a division of application No. 09/707,022, filed on Nov. 6, 2000, now Pat. No. 6,758,824.

(51) Int. Cl.
    *A61B 10/00* (2006.01)
(52) U.S. Cl. ...................................... 600/565
(58) Field of Classification Search ............ 600/562, 600/564, 565, 566, 568
    See application file for complete search history.

(56) References Cited

U.S. PATENT DOCUMENTS

| | | | |
|---|---|---|---|
| 1,337,733 A | 4/1920 | Sweetland et al. | |
| 1,693,741 A | 12/1928 | Wuest | |
| 1,734,652 A | 11/1929 | Sweetland | |
| 1,941,982 A | 1/1934 | Gill | |
| 2,047,714 A | 7/1936 | Smith | |
| 2,656,930 A | 10/1953 | DeVries | |
| 2,689,048 A | 9/1954 | Powers | |

(Continued)

FOREIGN PATENT DOCUMENTS

DE            9112550         11/1991

(Continued)

OTHER PUBLICATIONS

CA Publication in Design News entitled "Probe reduces breast biopsy trauma" by Joseph Ogando dated Aug. 7, 2000.

(Continued)

*Primary Examiner* — Max Hindenburg
*Assistant Examiner* — Michael C Stout
(74) *Attorney, Agent, or Firm* — Vista IP Law Group LLP

(57) ABSTRACT

A method of relieving vacuum in a biopsy apparatus includes applying vacuum through at least one motor to an inner cannula lumen; providing a continuously open leak path that permits fluid communication between the outer cannula lumen and atmosphere, wherein fluid is drawn from the leak path through the outer cannula; retracting the inner cannula proximally to permit tissue to prolapse into a tissue receiving opening of the outer cannula due to the vacuum; translating the inner cannula distally to sever the prolapsed tissue; aspirating the severed tissue through the inner cannula lumen; and selectively relieving vacuum distally of the severed tissue by retracting the inner cannula proximally to permit the inner cannula lumen to communicate with the respective outer cannula lumen and the leak path while a portion of the biopsy apparatus, including the tissue receiving opening, is positioned within tissue.

8 Claims, 7 Drawing Sheets

U.S. PATENT DOCUMENTS

| | | | |
|---|---|---|---|
| 3,401,684 A | 9/1968 | Dremann | |
| 3,456,806 A | 7/1969 | Borston | |
| 3,561,429 A | 2/1971 | Jewett et al. | |
| 3,606,878 A | 9/1971 | Kellogg | |
| 3,785,380 A | 1/1974 | Brumfield | |
| 3,815,604 A | 6/1974 | O'Malley et al. | |
| 3,833,000 A | 9/1974 | Bridgman | |
| 3,889,657 A | 6/1975 | Baumgarten | |
| 3,890,712 A | 6/1975 | Lopez | |
| 3,937,222 A | 2/1976 | Banko | |
| 3,938,505 A | 2/1976 | Jamshidi | |
| 3,945,375 A | 3/1976 | Banko | |
| 3,994,297 A | 11/1976 | Kopf | |
| 4,007,742 A | 2/1977 | Banko | |
| D243,559 S | 3/1977 | Hoyle et al. | |
| 4,019,514 A | 4/1977 | Banko | |
| 4,083,706 A | 4/1978 | Wiley | |
| 4,101,756 A | 7/1978 | Yamano | |
| 4,117,843 A | 10/1978 | Banko | |
| 4,159,773 A | 7/1979 | Losenno | |
| 4,167,943 A | 9/1979 | Banko | |
| 4,167,944 A | 9/1979 | Banko | |
| 4,177,814 A | 12/1979 | Knepshield et al. | |
| 4,210,146 A | 7/1980 | Banko | |
| 4,220,252 A | 9/1980 | Beall et al. | |
| 4,221,225 A | 9/1980 | Sloan et al. | |
| 4,257,425 A | 3/1981 | Ryan | |
| 4,282,098 A | 8/1981 | Morgan, Jr. | |
| 4,308,878 A | 1/1982 | Silva | |
| 4,316,465 A | 2/1982 | Dotson, Jr. | |
| 4,354,093 A | 10/1982 | Zago | |
| 4,368,734 A | 1/1983 | Banko | |
| 4,382,808 A | 5/1983 | Van Wormer, Jr. et al. | |
| 4,468,217 A | 8/1984 | Kuzmick et al. | |
| 4,513,745 A | 4/1985 | Amoils | |
| 4,530,356 A | 7/1985 | Helfgott et al. | |
| 4,533,818 A | 8/1985 | Green | |
| 4,549,554 A | 10/1985 | Markham | |
| 4,562,838 A | 1/1986 | Walker | |
| 4,644,951 A | 2/1987 | Bays | |
| 4,651,753 A | 3/1987 | Lifton | |
| 4,662,869 A * | 5/1987 | Wright | 604/22 |
| 4,696,298 A | 9/1987 | Higgins et al. | |
| 4,708,147 A | 11/1987 | Haaga | |
| 4,803,341 A | 2/1989 | Barowski et al. | |
| 4,817,631 A | 4/1989 | Schnepp-Pesch et al. | |
| 4,838,280 A * | 6/1989 | Haaga | 600/564 |
| 4,850,373 A | 7/1989 | Zatloukal et al. | |
| 4,871,074 A | 10/1989 | Bryson et al. | |
| 4,886,492 A | 12/1989 | Brooke et al. | |
| 4,893,635 A | 1/1990 | de Groot et al. | |
| 4,919,146 A | 4/1990 | Rhinehart et al. | |
| 4,926,877 A | 5/1990 | Bookwalter | |
| RE33,258 E | 7/1990 | Onik et al. | |
| 4,973,019 A | 11/1990 | Baird et al. | |
| 4,985,027 A | 1/1991 | Dressel | |
| 4,989,614 A | 2/1991 | Dejter, Jr. et al. | |
| 5,027,827 A | 7/1991 | Cody et al. | |
| 5,031,778 A | 7/1991 | Edgecombe | |
| 5,047,008 A * | 9/1991 | de Juan et al. | 604/22 |
| 5,052,999 A | 10/1991 | Klein | |
| 5,054,615 A | 10/1991 | Stillwagon et al. | |
| 5,074,311 A | 12/1991 | Hasson | |
| 5,080,869 A | 1/1992 | McCormick | |
| 5,090,649 A | 2/1992 | Tipp | |
| 5,108,381 A | 4/1992 | Kolozsi | |
| 5,124,532 A | 6/1992 | Hafey et al. | |
| 5,141,189 A | 8/1992 | Andrew | |
| D329,304 S | 9/1992 | Tipp | |
| 5,172,701 A | 12/1992 | Leigh | |
| D332,670 S | 1/1993 | McFarland | |
| 5,176,677 A * | 1/1993 | Wuchinich | 606/46 |
| 5,183,052 A | 2/1993 | Terwilliger | |
| 5,192,439 A | 3/1993 | Roth et al. | |
| 5,197,968 A | 3/1993 | Clement | |
| 5,213,110 A | 5/1993 | Kedem et al. | |
| 5,243,994 A | 9/1993 | Ranalletta | |
| D342,585 S | 12/1993 | Fischbach et al. | |
| 5,275,609 A | 1/1994 | Pingleton et al. | |
| 5,284,156 A | 2/1994 | Schramm et al. | |
| 5,284,472 A | 2/1994 | Sussman et al. | |
| 5,285,795 A | 2/1994 | Ryan et al. | |
| 5,295,980 A | 3/1994 | Ersek | |
| 5,348,022 A | 9/1994 | Leigh et al. | |
| 5,358,638 A | 10/1994 | Gershenson | |
| 5,403,276 A | 4/1995 | Schechter et al. | |
| 5,411,513 A | 5/1995 | Ireland et al. | |
| 5,423,844 A | 6/1995 | Miller | |
| 5,429,138 A | 7/1995 | Jamshidi | |
| 5,429,596 A | 7/1995 | Arias et al. | |
| 5,456,267 A | 10/1995 | Stark | |
| 5,458,112 A | 10/1995 | Weaver | |
| 5,464,300 A | 11/1995 | Crainich | |
| 5,505,210 A * | 4/1996 | Clement | 600/566 |
| 5,520,635 A | 5/1996 | Gelbfish | |
| 5,520,801 A | 5/1996 | Gerber et al. | |
| D371,220 S | 6/1996 | Behrens | |
| 5,526,822 A | 6/1996 | Burbank et al. | |
| 5,533,642 A | 7/1996 | Lafond et al. | |
| 5,543,114 A | 8/1996 | Dudek | |
| 5,575,293 A | 11/1996 | Miller et al. | |
| 5,580,347 A | 12/1996 | Reimels | |
| D377,996 S | 2/1997 | Gilbert | |
| 5,615,782 A | 4/1997 | Choe | |
| D379,554 S | 5/1997 | Landers | |
| 5,630,939 A | 5/1997 | Bulard et al. | |
| 5,643,304 A | 7/1997 | Schechter et al. | |
| 5,649,547 A | 7/1997 | Ritchart et al. | |
| 5,669,876 A | 9/1997 | Schechter et al. | |
| 5,669,923 A | 9/1997 | Gordon | |
| D386,818 S | 11/1997 | Boomfield | |
| 5,685,838 A | 11/1997 | Peters et al. | |
| 5,685,840 A | 11/1997 | Schechter et al. | |
| 5,730,717 A | 3/1998 | Gelbfish | |
| 5,769,086 A | 6/1998 | Ritchart et al. | |
| 5,775,333 A | 7/1998 | Burbank et al. | |
| 5,779,649 A | 7/1998 | Herbert | |
| 5,782,849 A | 7/1998 | Miller | |
| 5,788,651 A | 8/1998 | Weilandt | |
| 5,794,626 A | 8/1998 | Kieturakis | |
| 5,794,799 A | 8/1998 | Collins et al. | |
| 5,807,275 A * | 9/1998 | Jamshidi | 600/567 |
| 5,810,806 A | 9/1998 | Ritchart et al. | |
| 5,843,111 A | 12/1998 | Vijfvinkel | |
| 5,848,978 A | 12/1998 | Cecchi | |
| D403,810 S | 1/1999 | Owens | |
| 5,893,862 A | 4/1999 | Pratt et al. | |
| 5,911,701 A | 6/1999 | Miller et al. | |
| 5,913,857 A | 6/1999 | Ritchart et al. | |
| 5,916,229 A | 6/1999 | Evans | |
| 5,928,164 A | 7/1999 | Burbank et al. | |
| 5,928,218 A | 7/1999 | Gelbfish | |
| 5,944,673 A | 8/1999 | Gregoire et al. | |
| 5,964,716 A | 10/1999 | Gregoire et al. | |
| 5,971,939 A | 10/1999 | DeSantis et al. | |
| 5,980,469 A | 11/1999 | Burbank et al. | |
| 5,980,545 A | 11/1999 | Pacala et al. | |
| 5,980,546 A | 11/1999 | Hood | |
| 5,997,560 A | 12/1999 | Miller | |
| 6,007,497 A | 12/1999 | Huitema | |
| 6,017,316 A * | 1/2000 | Ritchart et al. | 600/567 |
| 6,019,733 A | 2/2000 | Farascioni | |
| 6,022,324 A | 2/2000 | Skinner | |
| D423,717 S | 4/2000 | Taylor | |
| 6,050,955 A | 4/2000 | Bryan et al. | |
| D426,025 S | 5/2000 | Holmes et al. | |
| 6,077,230 A | 6/2000 | Gregoire et al. | |
| 6,080,113 A | 6/2000 | Heneveld et al. | |
| 6,085,749 A | 7/2000 | Wardle et al. | |
| 6,086,544 A * | 7/2000 | Hibner et al. | 600/568 |
| 6,096,042 A | 8/2000 | Herbert | |
| 6,109,446 A | 8/2000 | Foote | |
| 6,120,462 A | 9/2000 | Hibner et al. | |
| 6,120,463 A | 9/2000 | Bauer | |
| 6,123,299 A | 9/2000 | Zach, Sr. | |
| 6,142,955 A | 11/2000 | Farascioni et al. | |
| 6,148,857 A | 11/2000 | West et al. | |

| | | | |
|---|---|---|---|
| 6,162,187 | A | 12/2000 | Buzzard et al. |
| 6,193,414 | B1 | 2/2001 | Balzano |
| 6,193,673 | B1 | 2/2001 | Voila et al. |
| 6,261,302 | B1 | 7/2001 | Voegele et al. |
| 6,273,862 | B1 | 8/2001 | Privitera et al. |
| 6,293,957 | B1 | 9/2001 | Peters et al. |
| 6,331,165 | B1 | 12/2001 | Turturro et al. |
| 6,346,107 | B1 | 2/2002 | Cucin |
| 6,379,372 | B1 | 4/2002 | Dehdashtian et al. |
| 6,402,701 | B1 | 6/2002 | Kaplan et al. |
| 6,428,487 | B1 | 8/2002 | Burdorff et al. |
| 6,461,350 | B1 | 10/2002 | Underwood et al. |
| 6,468,225 | B1 | 10/2002 | Lundgren |
| 6,468,227 | B2 | 10/2002 | Zimmon |
| 6,471,700 | B1 | 10/2002 | Burbank et al. |
| 6,485,436 | B1 * | 11/2002 | Truckai et al. ............... 600/564 |
| 6,592,508 | B1 | 7/2003 | Ravins et al. |
| 6,632,182 | B1 | 10/2003 | Treat |
| 6,638,235 | B2 | 10/2003 | Miller et al. |
| 6,743,245 | B2 | 6/2004 | Lobdell |
| 6,752,768 | B2 | 6/2004 | Burdorff et al. |
| 6,758,824 | B1 * | 7/2004 | Miller et al. ............... 600/568 |
| 6,951,611 | B2 | 10/2005 | Dannenmaier et al. |
| 7,041,217 | B1 | 5/2006 | Close et al. |
| 7,226,424 | B2 | 6/2007 | Ritchart et al. |
| 7,316,726 | B2 | 1/2008 | Schwindt |
| 7,867,173 | B2 * | 1/2011 | Hibner et al. ............... 600/568 |
| 2001/0014785 | A1 | 8/2001 | Sussman et al. |
| 2002/0045840 | A1 | 4/2002 | Voegele et al. |
| 2002/0077565 | A1 | 6/2002 | Burdorff et al. |
| 2002/0082519 | A1 * | 6/2002 | Miller et al. ............... 600/566 |
| 2002/0120212 | A1 | 8/2002 | Ritchart et al. |
| 2002/0138047 | A1 | 9/2002 | Lopez |
| 2002/0156365 | A1 | 10/2002 | Tsekos |
| 2003/0018281 | A1 | 1/2003 | Huitema |
| 2003/0073929 | A1 | 4/2003 | Baltschun et al. |
| 2003/0087423 | A1 | 5/2003 | Haywood et al. |
| 2004/0049128 | A1 | 3/2004 | Miller et al. |
| 2004/0222137 | A1 | 11/2004 | Hashimoto |
| 2004/0222145 | A1 | 11/2004 | Onoue et al. |
| 2005/0049521 | A1 * | 3/2005 | Miller et al. ............... 600/565 |
| 2005/0113715 | A1 | 5/2005 | Schwindt et al. |
| 2006/0155210 | A1 | 7/2006 | Beckman et al. |
| 2007/0032741 | A1 * | 2/2007 | Hibner et al. ............... 600/566 |
| 2009/0171242 | A1 * | 7/2009 | Hibner ............... 600/566 |

FOREIGN PATENT DOCUMENTS

| | | |
|---|---|---|
| EP | 0541970 | 5/1993 |
| WO | WO-0197702 | 12/2001 |

OTHER PUBLICATIONS

International Search Report No. PCT/US01/51235 dated Dec. 10, 2002.
Steven K. Wagner, "Imaging News," Breast ultrasound spurs biopsy technology race, (Mar. 6, 1996).
Publication in Design News entitled "Probe reduces breast biopsy trauma" by Joseph Ogando dated Aug. 7, 2000.
International Search Report No. PCT/US01/51235.
International Search Report PCT/US207/061910 dated Nov. 6, 2007.
WebMd Medical Dictiionary "What is Tissue?" 2006, http://dictionary.webmd.com/terms/tissue.xml.
Blood: definition, usage and pronunciation, YourDictionary.com, http://www.yourdictionary.com/blood.
Blood-definnition from Biology-Online.org, Oct. 3, 2005, http://www.biology-online.org/dictionary/Blood.
Eionet GEMET Thesaurus, "blood (tissue)", Oct. 17, 2007, http://www.eionet.europa.eu/gemet/concept?cp=935.
Biology 20-Investigation "Blood Tissue", www.blackgold.ab.ca/microtest/Biology 20 Labs/blood_tissue.pdf.
Office Action for U.S. Appl. No. 10/958,026 dated Jan. 10, 2005 (9 pages).
Amendment to Office Action for U.S. Appl. No. 10/958,026 dated Jan. 10, 2005. (7 pages).
Notice of Non-Compliant Amendment for U.S. Appl. No. 10/958,206 dated Apr. 20, 2005 (2 pages).
Response to Non-Compliant Notice of Apr. 20, 2005 for U.S. Appl. No. 10/958,026 (6 pages).
Final Office Action for U.S. Appl. No. 10/958,026 dated Aug. 9, 2005. (6 pages).
Response to Final Office Action dated Aug. 9, 2005 for U.S. Appl. No. 10/958,026 (7 pages).
Advisory Action dated Nov. 2, 2005 for U.S. Appl. No. 10/958,026 (3 pages).
Request for Continued Examination filed in response to Nov. 2, 2005 Advisory Action for U.S. Appl. No. 10/958,026 (5 pages).
Office Action dated Dec. 23, 2005 for U.S. Appl. No. 10/958,026 (8 pages).
Response to Office Action dated Dec. 23, 2005 for U.S. Appl. No. 10/958,026 (7 pages).
Office Action dated Oct. 26, 2006 for U.S. Appl. No. 10/958,026 (7 pages).
Response to Office Action dated Oct. 26, 2006 for U.S. Appl. No. 10/958,026 (8 pages).
Advisory Action dated Jan. 16, 2007 for U.S. Appl. No. 10/958,026 (3 pages).
Request for Continued Examination filed in response to Advisory Action dated Jan. 16, 2007 for U.S. Appl. No. 10/958,026 (4 pages).
Office Action dated Mar. 7, 2007 for U.S. Appl. No. 10/958,026 (10 pages).
Response to Office Action dated Mar. 7, 2007 for U.S. Appl. No. 10/958,026 (17 pages).
Office Action dated Aug. 17, 2007 for U.S. Appl. No. 10/958,026 (8 pages).
RCE & Response to Office Action dated Aug. 17, 2007 for U.S. Appl. No. 10/958,026 (13 pages).
Office Action dated Dec. 21, 2007 for U.S. Appl. No. 10/958,026 (9 pages).
Response to Office Action dated Dec. 21, 2007 for U.S. Appl. No. 10/958,026 (16 pages).
Office Action dated Aug. 16, 2007 for U.S. Appl. No. 11/132,034 (21 pages).
Response to Office Action dated Nov. 16, 2007 for U.S. Appl. No. 11/132,034 (20 pages).
Office Action dated Feb. 1, 2008 for U.S. Appl. No. 11/132,034 (17 pages).
Response to Office Action dated Feb. 1, 2008 for U.S. Appl. No. 11/132,034 (18 pages).
Final Office Action dated Jul. 9, 2008 for U.S. Appl. No. 10/958,026 (17 Pages).
Non-Final Office Action dated Nov. 7, 2008 for U.S. Appl. No. 10/639,569 (11 pages).
English Abract for EP0536549 related to DE9112550 to Wolf.
Amendment to Office Action for U.S. Appl. No. 10/958,026 dated Sep. 30, 2008.
Advisory Action for U.S. Appl. No. 10/958,026 dated Oct. 17, 2008.
Request for Continued Examination for U.S. Appl. No. 10/958,206, filed Nov. 7, 2008.
Office Action for U.S. Appl. No. 11/364,123 dated Apr. 14, 2008.
Amendment to Office Action for U.S. Appl. No. 11/364,123 dated Jul. 14, 2008.
Office Action for U.S. Appl. No. 11/364,123 dated Oct. 30, 2008.
Amendment and Request for Continued Examination for U.S. Appl. No. 10/639,569 dated Oct. 26, 2007.
Non-Final Office Action for U.S. Appl. No. 10/639,569 dated Mar. 16, 2006.
Amendment to Non-Final Office Action for U.S. Appl. No. 10/639,569 dated Jun. 16, 2006.
Final Office Acton for U.S. Appl. No. 10/639,569 dated Oct. 30, 2006.
Amendment and Request for Continued Examination for U.S. Appl. No. 10/639,569 dated Dec. 27, 2006.
Non-Final Office Action for U.S. Appl. No. 10/639,569 dated Apr. 11, 2007.
Amendment to Non-Final Office Action for U.S. Appl. No. 10/639,569 dated Nov. 10, 2007.
Final Office Aciton for U.S. Appl. No. 10/639,569 dated Sep. 18, 2007.
Office Acton dated Mar. 21, 2008 for U.S. Appl. No. 11/247,707.

Amendment to Office Action dated Mar. 21, 2008 for U.S. Appl. No. 11/247,707.
Final Office Action dated Oct. 10, 2008 for U.S. Appl. No. 11/247,707.
RCE & Amendment to Final OA dated Oct. 10, 2008 for U.S. Appl. No. 11/247,707.
RCE & Amendment After Final dated Oct. 26, 2007 for U.S. Appl. No. 10/639,569.
Amendment to Non-Final Office Action dated Jan. 26, 2009 for U.S. Appl. No. 10/639,569.
Office Action dated Dec. 26, 2008 for U.S. Appl. No. 10/958,026.
Office Action dated Jun. 9, 2006 for U.S. Appl. No. 10/970,269.
Amendment to Non-Final OA of Jun. 9, 2006 for U.S. Appl. No. 10/970,269.
Office Action dated Nov. 27, 2006 for U.S. Appl. No. 10/970,269.
Amendment to Non-Final OA of Nov. 27, 2006 for U.S. Appl. No. 10/970,269.
Final OA dated Sep. 18, 2007 for U.S. Appl. No. 10/970,269.
Advisory Action dated Sep. 18, 2007 for U.S. Appl. No. 10/970,269.
RCE & Amendment AF dated Jan. 8, 2008 for U.S. Appl. No. 10/970,269.
Office Action dated Mar. 4, 2008 for U.S. Appl. No. 10/970,269.
Amendment to Non-Final OA dated Mar. 4, 2008 for U.S. Appl. No. 10/970,269.
Interview Summary dated Jun. 4, 2008 for U.S. Appl. No. 10/970,269.
Amendment in Response to Examiner's Interview Summary of Jun. 4, 2008 for U.S. Appl. No. 10/970,269.
Office Action for U.S. Appl. No. 10/848,278 dated Jul. 1, 2008.
Amendment to Office Action for U.S. Appl. No. 10/848,278 dated Sep. 25, 2008.
Response to Non-Compliant Amendment to U.S. Appl. No. 10/848,278 dated Oct. 17, 2008.
Final Office Aciton for U.S. Appl. No. 10/848,278 dated Nov. 6, 2008.
Amendment After Final for U.S. Appl. No. 10/848,278 dated Dec. 17, 2008.
Advisory Action for U.S. Appl. No. 10/848,278 dated Jan. 6, 2009.
Final Office Action dated Jan. 23, 2009 for U.S. Appl. No. 11/132,034.
Amendment in response to Final Office Action dated Jan. 23, 2009 for U.S. Appl. No. 11/132,034.
Notice of Allowance dated Apr. 8, 2009 for U.S. Appl. No. 11/132,034.
Office Action dated Feb. 26, 2009 for U.S. Appl. No. 11/247,707.
Office Aciton dated Mar. 4, 2009 for U.S. Appl. No. 10/848,278.
Office Aciton dated Mar. 24, 2009 for U.S. Appl. No. 11/364,123.
Office Action dated Apr. 7, 2009 for U.S. Appl. No. 10/639,569.
Amendment to Office Action dated Mar. 4, 2009 for U.S. Appl. No. 10/848,278.
Amendment in response to Office Action dated Apr. 7, 2009 for U.S. Appl. No. 10/639,569.
Amendment in response to Office Action dated Mar. 24, 2009 for U.S. Appl. No. 11/364,123.
Response to Final Office Action dated Oct. 27, 2009 for U.S. Appl. No. 11/364,123.
Office Action dated Dec. 15, 2009 for U.S. Appl. No. 10/848,278.
Response to Office Action dated Oct. 26, 2009 for U.S. Appl. No. 11/351,917.
Response to Office Action dated Nov. 10, 2010 for U.S. Appl. No. 10/639,569.
Notice of Allowance dated Oct. 8, 2008 for U.S. Appl. No. 10/970,269.
Non-Final Office Action dated Feb. 24, 2010 for U.S. Appl. No. 11/364,123.
Response to Non-Final Office Action dated Dec. 15, 2009 for U.S. Appl. No. 10/848,278.
Final Office Action dated Apr. 27, 2010 for U.S. Appl. No. 11/351,917.
Final Office Action dated Apr. 29, 2010 for U.S. Appl. No. 10/639,569.
Response to Non-Final Office Action dated Feb. 24, 2010 for U.S. Appl. No. 11/364,123.
Response to Office Action dated Apr. 27, 2010 for U.S. Appl. No. 11/351,917.
Final Office Action dated Jun. 8, 2010 for U.S. Appl. No. 10/848,278.
Response to Final Office Action dated Apr. 29, 2010 for U.S. Appl. No. 10/639,569.
Notice of Allowance dated Jul. 12, 2010 for U.S. Appl. No. 11/351,917.
Final Office Action dated Jul. 23, 2010 for U.S. Appl. No. 11/364,123.
Response to Final Office Action dated Jun. 8, 2010 for U.S. Appl. No. 10/848,278.
Response to Final Office Action dated Jul. 23, 2010 for U.S. Appl. No. 11/364,123.
Non-Final Office Action dated Sep. 28, 2010 for U.S. Appl. No. 10/848,278.
Notice of Allowance issued on Sep. 29, 2010 for U.S. Appl. No. 11/364,123.
Non-Final Office Action dated Oct. 27, 2010 for U.S. Appl. No. 10/639,569.
Response to Non-Final Office Action dated Oct. 27, 2010 for U.S. Appl. No. 10/639,569.
Reponse to Non-Final Office Action dated Sep. 28, 2010 for U.S. Appl. No. 10/848,278.
Non-Final Office Action dated Mar. 23, 2011 for U.S. Appl. No. 10/639,569.
Final Office Action dated Mar. 21, 2011 for U.S. Appl. No. 10/848,278.
Response to Final Office Action dated Mar. 21, 2011 for U.S. Appl. No. 10/848,278.
Response to Non-Final Office Action dated Mar. 23, 2011 for U.S. Appl. No. 10/639,569.
Office Action dated Aug. 26, 2009 for U.S. Appl. No. 10/848,278.
Response to Office Action dated Aug. 26, 2009 for U.S. Appl. No. 10/848,278.
Office Action dated Oct. 26, 2009 for U.S. Appl. No. 11/351,917.
Final Office Action dated Oct. 27, 2009 for U.S. Appl. No. 11/364,123.
Office Action dated Nov. 10, 2009 for U.S. Appl. No. 10/639,569.

* cited by examiner

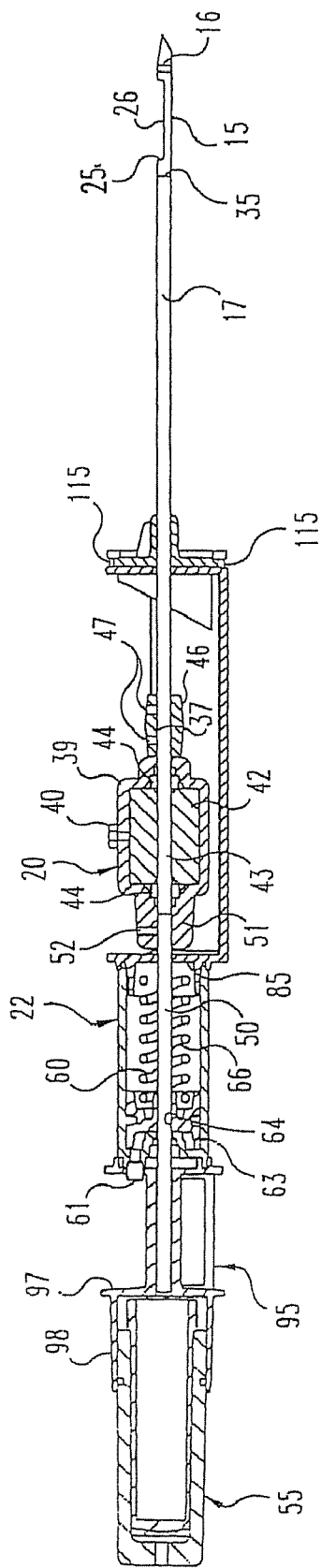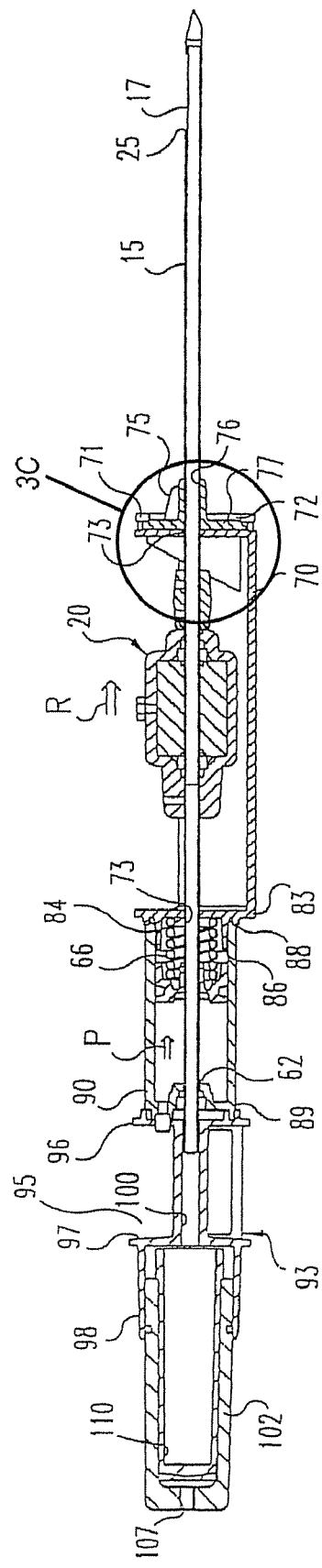
FIG. 3A
FIG. 3B

BIOPSY APPARATUS WITH VACUUM RELIEF

CROSS-REFERENCE TO RELATED APPLICATIONS

This application is a Divisional of application Ser. No. 10/970,269 filed on Oct. 21, 2004, which is a Continuation of application Ser. No. 10/848,278 filed on May 18, 2004 which is a Divisional of application Ser. No. 09/707,022 filed Nov. 6, 2000, now U.S. Pat. No. 6,758,824; and this application is related to application Ser. No. 10/639,569 filed Aug. 12, 2003 which is a Divisional of application Ser. No. 09/864,031 filed on May 23, 2001, now U.S. Pat. No. 6,638,235, which is a Continuation-in-Part of application Ser. No. 09/707,022 filed Nov. 6, 2000, now U.S. Pat. No. 6,758,824, which are incorporated herein by reference in their entirety.

TECHNICAL FIELD

This invention relates to biopsy instruments and methods for taking a biopsy. More specifically, this invention relates to a method for removing several tissue samples using a single insertion.

BACKGROUND

In the diagnosis and treatment of breast cancer, it is often necessary to remove multiple tissue samples from a suspicious mass. The suspicious mass is typically discovered during a preliminary examination involving visual examination, palpitation, X-ray, MRI, ultrasound imaging or other detection means. When this preliminary examination reveals a suspicious mass, the mass must be evaluated by taking a biopsy in order to determine whether the mass is malignant or benign. Early diagnosis of breast cancer, as well as other forms of cancer, can prevent the spread of cancerous cells to other parts of the body and ultimately prevent fatal results.

A biopsy can be performed by either an open procedure or a percutaneous method. The open surgical biopsy procedure first requires localization of the lesion by insertion of a wire loop, while using visualization technique, such as X-ray or ultrasound. Next, the patient is taken to a surgical room where a large incision is made in the breast, and the tissue surrounding the wire loop is removed. This procedure causes significant trauma to the breast tissue, often leaving disfiguring results and requiring considerable recovery time for the patient. This is often a deterrent to patients receiving the medical care they require. The open technique, as compared to the percutaneous method, presents increased risk of infection and bleeding at the sample site. Due to these disadvantages, percutaneous methods are often preferred.

Percutaneous biopsies have been performed using either Fine Needle Aspiration or core biopsy in conjunction with real-time visualization techniques, such as ultrasound or mammography (X-ray). Fine Needle Aspiration involves the removal of a small number of cells using an aspiration needle. A smear of the cells is then analyzed using cytology techniques. Although Fine Needle Aspiration is less intrusive, only a small amount of cells are available for analysis. In addition, this method does not provide for a pathological assessment of the tissue, which can provide a more complete assessment of the stage of the cancer, if found. In contrast, in core biopsy a larger fragment of tissue can be removed without destroying the structure of the tissue. Consequently, core biopsy samples can be analyzed using a more comprehensive histology technique, which indicates the stage of the cancer. In the case of small lesions, the entire mass may be removed using the core biopsy method. For these reasons core biopsy is preferred, and there has been a trend towards the core biopsy method, so that a more detailed picture can be constructed by pathology of the disease's progress and type.

The first core biopsy devices were of the spring advanced, "Tru-Cut" style consisting of a hollow tube with a sharpened edge that was inserted into the breast to obtain a plug of tissue. This device presented several disadvantages. First, the device would sometimes fail to remove a sample, therefore, requiring additional insertions. This was generally due to tissue failing to prolapse into the sampling notch. Secondly, the device had to be inserted and withdrawn to obtain each sample, therefore, requiring several insertions in order to acquire sufficient tissue for pathology.

The biopsy apparatus disclosed in U.S. Pat. No. 5,526,822 to Burbank, et al was designed in an attempt to solve many of these disadvantages. The Burbank apparatus is a biopsy device that requires only a single insertion into the biopsy site to remove multiple tissue samples. The device incorporates a tube within a tube design that includes an outer piercing needle having a sharpened distal end for piercing the tissue. The outer needle has a lateral opening forming a tissue receiving port. The device has an inner cannula slidingly disposed within the outer cannula, and which serves to cut tissue that has prolapsed into the tissue receiving port. Additionally, a vacuum is used to draw the tissue into the tissue receiving port.

Although the Burbank device presented an advancement in the field of biopsy devices, several disadvantages remain and further improvements are needed. For example, the inner cutter must be advanced manually, meaning the surgeon manually moves the cutter back and forth by lateral movement of a knob mounted on the outside of the instrument or by one of the three pedals at the footswitch. Also, the vacuum source that draws the tissue into the receiving port is typically supplied via a vacuum chamber attached to the outer cannula. The vacuum chamber defines at least one, usually multiple, communicating holes between the chamber and the outer cannula. These small holes often become clogged with blood and bodily fluids. The fluids occlude the holes and prevent the aspiration from drawing the tissue into the receiving port. This ultimately prevents a core from being obtained, a condition called a "dry tap." In light of the foregoing disadvantages, a need remains for a method of tissue removal that reliably applies a vacuum.

BRIEF SUMMARY

A method of relieving vacuum in a biopsy apparatus that comprises an outer cannula defining a first inner lumen therethrough and a tissue-receiving opening in communication with the first inner lumen; an inner cannula slidably disposed in the first inner lumen of the outer cannula, wherein the inner cannula defines a second inner lumen therethrough, at least one motor for moving the inner cannula relative to the outer cannula, and a vacuum source in fluid communication with the second inner lumen of the inner cannula, is disclosed. The method comprises applying vacuum from the vacuum source to the second inner lumen of the inner cannula; providing a leak path that permits fluid communication between the first inner lumen of the outer cannula and the atmosphere at a proximal end of the outer cannula; retracting the inner cannula away from a distal end of the outer cannula so as to permit tissue to prolapse into the tissue receiving opening due to the vacuum created through the second inner lumen of the inner cannula; translating the inner cannula toward the distal end of the outer cannula to sever the tissue that has prolapsed into the tissue receiving opening; aspirating the severed tissue through the second inner lumen of the inner cannula; and selectively relieving vacuum distally of the severed and aspirating tissue. The vacuum relief is achieved by retracting the inner cannula away from the distal end of said outer cannula thereby permitting the second inner lumen to communicate with the first inner lumen and the leak path while a portion of the biopsy apparatus, including the tissue receiving opening, is positioned within tissue.

BRIEF DESCRIPTION OF THE DRAWINGS

FIG. 3A and FIG. 3B are side cross-sectional views of the tissue biopsy apparatus depicted in FIGS. 1 and 2, with the tissue cutting inner cannula shown in its retracted and extended positions.

DETAILED DESCRIPTION

Figure 1:
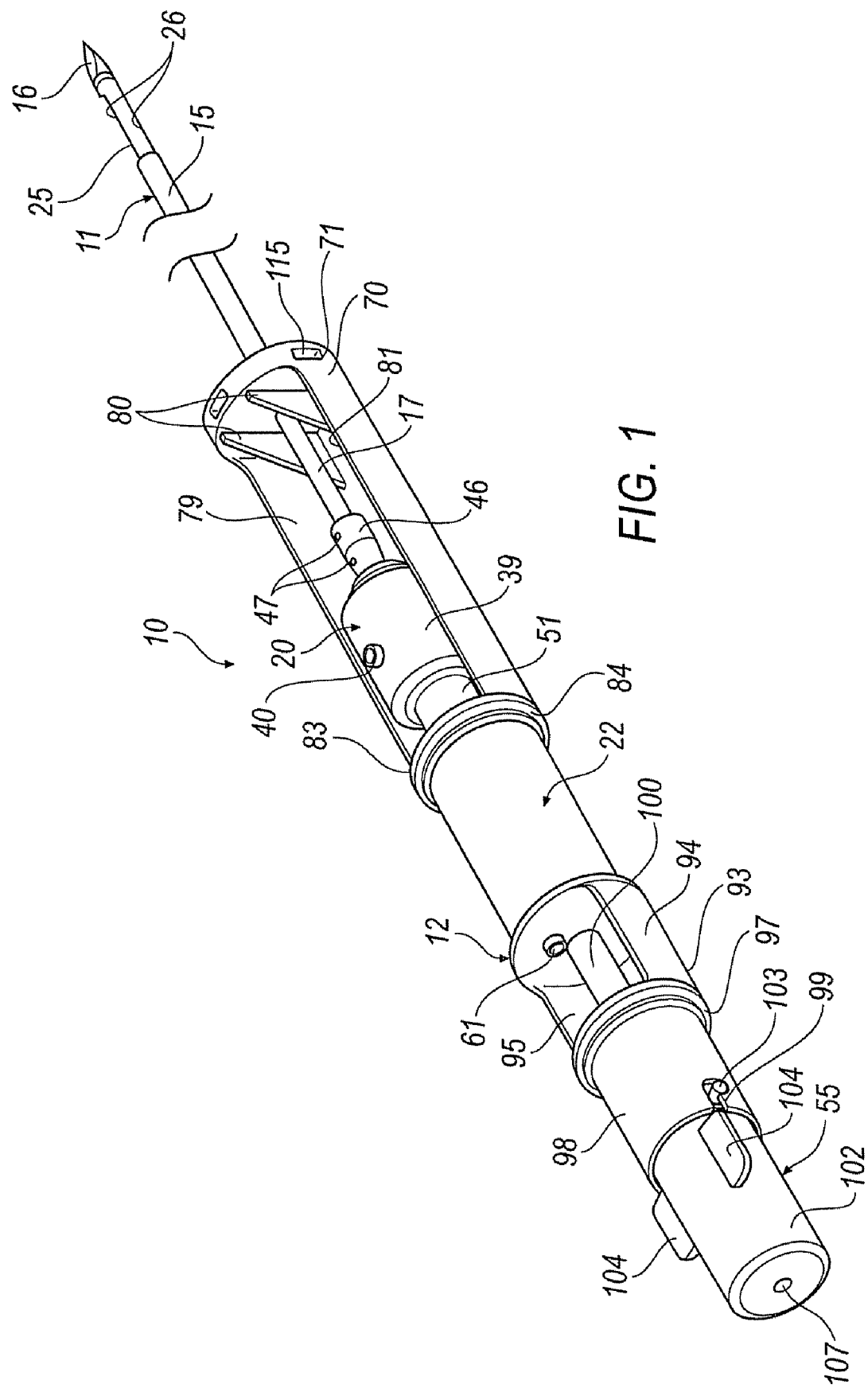
FIG. 1 is a top perspective view of a tissue biopsy apparatus in accordance with one embodiment of the present invention
Figure 2:
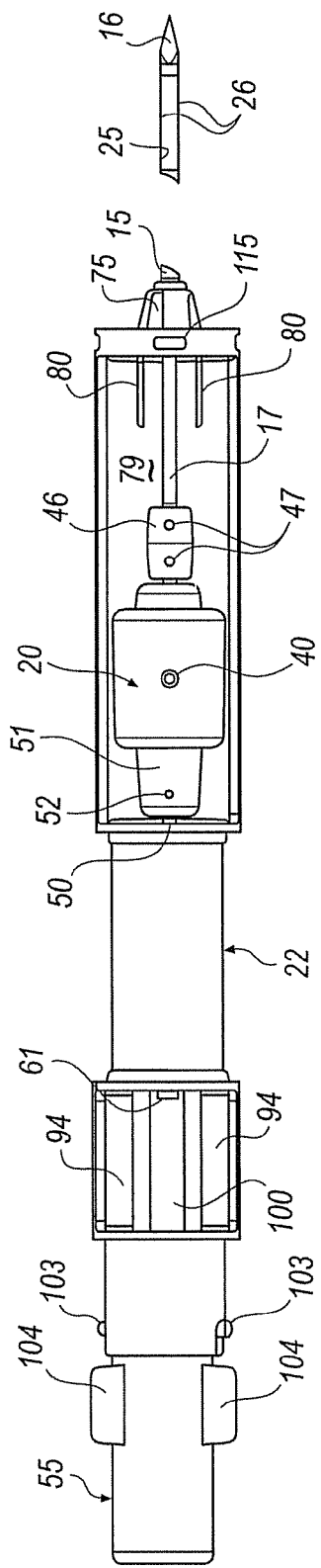
FIG. 2 is a top elevational view of the tissue biopsy apparatus shown in FIG. 1.
Figure 3C:
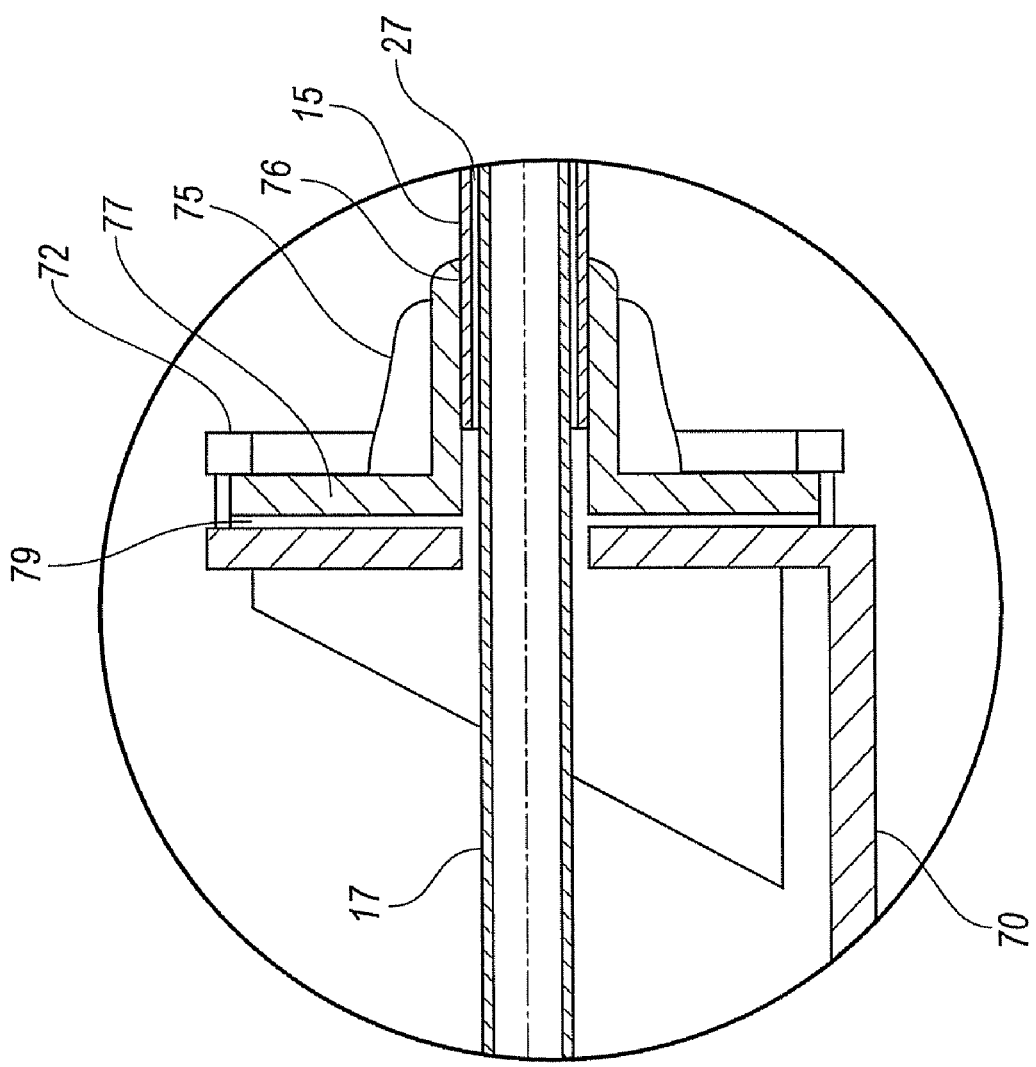
FIG. 3C is an enlarged view of encircled area 3C taken from FIG. 3B.

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

A tissue biopsy apparatus 10 in accordance with one embodiment of the present invention is shown in FIGS. 1-5. The apparatus 10 includes a cutting element 11 mounted to a handpiece 12. The cutting element 11 is sized for introduction into a human body. Most particularly, the present invention concerns an apparatus for excising breast tissue samples. Thus, the cutting element 11 and the overall biopsy apparatus 10 are configured for ease of use in this surgical environment. In the illustrated embodiment, the biopsy apparatus 10 is configured as a hand-held device. However, the same inventive principles can be employed in a tissue biopsy apparatus that is used stereotatically in which the apparatus is mounted on a support fixture that is used to position the cutting element 11 relative to the tissue to be sampled. Nevertheless, for the purposes of understanding the present invention, the tissue biopsy apparatus will be described as a hand-held device.

The cutting element 11 is configured as "tube-within-a-tube" cutting device. More specifically, the cutting element 11 includes an outer cannula 15 terminating in a tip 16. Preferably, the tip is a trocar tip that can be used to penetrate the patient's skin. Alternatively, the tip 16 can simply operate as a closure for the open end of the cannula 15. In this instance, a separate introducer would be required.

The cutting element 11 further includes an inner cannula 17 that fits concentrically within the outer lumen 27 (FIG. 5) of the outer cannula 15. In the most preferred embodiment, both a rotary motor 20 (FIG. 1) and a reciprocating motor 22 drive the inner cannula 17. Both motors are supported within the handpiece 12. Again, in accordance with the preferred embodiment the rotary motor 20 and reciprocating motor 22 are configured for simultaneous operation to translate the inner cannula 17 axially within the outer cannula 15, while rotating the inner cannula 17 about its longitudinal axis.

Figure 5:
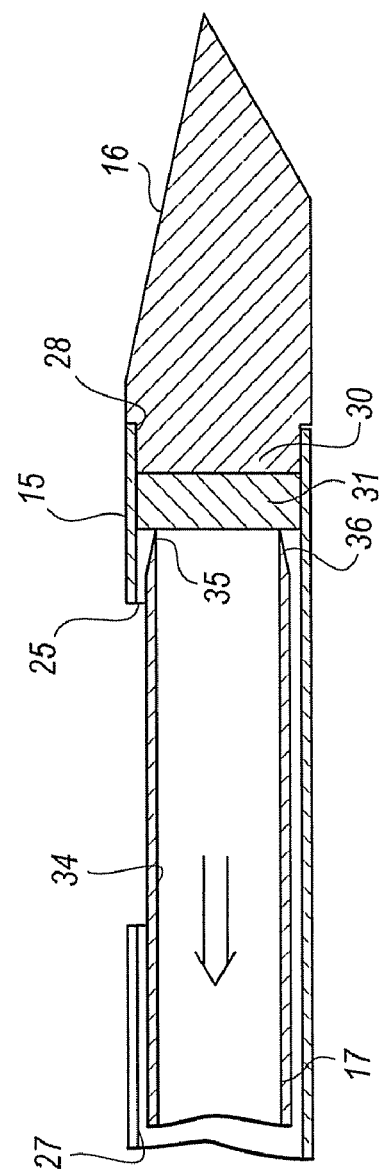
FIG. 5 is an enlarged side cross-sectional view of the operating end of the tissue biopsy apparatus depicted in FIGS. 1 and 2.

One specific configuration of the working end of the cutting element 11 is depicted in FIG. 5. The outer cannula 15 defines a tissue-receiving opening 25, which communicates with the outer lumen 27. A pair of opposite longitudinal edges 26 (FIGS. 1 and 2) define the tissue-receiving opening 25. The outer cannula 15 is open at its distal end 28 with the trocar tip 16 engaged therein. Preferably, the trocar tip 16 forms an engagement hub 30 that fits tightly within the distal end 28 of the outer cannula 15. The hub 30 can be secured by welding, press-fit, adhesive or other means suitable for a surgical biopsy instrument.

The working end of the cutting element 11 further includes a cuffing board 31 that is at least snugly disposed within the outer lumen 27 at the distal end 28 of the outer cannula 15. Most preferably, the cutting board 31 is in direct contact with the engagement hub 30 of the trocar tip 16. The cutting board 31 can be permanently affixed within the outer cannula 15 and/or against the engagement hub 30 of the trocar tip.

The inner cannula 17 defines an inner lumen 34 that is hollow along the entire length of the cannula to provide for aspiration of the biopsy sample. The inner cannula 17 terminates in a cutting edge 35. Preferably the cutting edge 35 is formed by an inwardly beveled surface 36 to provide a razor-sharp edge. The inwardly beveled surface helps eliminate the risk of catching the edge 35 on the tissue-receiving opening 25 of the outer cannula. In addition, the beveled surface 36 helps avoid pinching the biopsy material between the inner and outer cannulas during a cutting stroke.

In a specific embodiment, both the outer cannula 15 and the inner cannula 17 are formed of a surgical grade metal. Most preferably, the two cannulae are formed of stainless steel. In the case of an MRI compatible device, the cannulae can be formed of Inconel, Titanium or other materials with similar magnetic characteristics. Likewise, the trocar tip 16 is most preferably formed of stainless steel honed to a sharp tip. The trocar tip 16 can be suitably bounded to the outer cannula 15, such as by welding or the use of an appropriate adhesive.

The cutting board 31 is formed of a material that is configured to reduce the friction between the cutting edge 35 of the inner cannula 17 and the cutting board 31. The cutting edge 35 necessarily bears against the cutting board 31 when the inner cannula 17 is at the end of its stroke while severing a tissue sample. Since the inner cannula is also rotating, the cutting edge necessarily bears directly against the cutting board 31, particularly after the tissue sample has been cleanly severed. In prior devices, the impact-cutting surface has been formed of the same material as the cutting element. This leads to significant wear or erosion of the cutting edge. When numerous cutting cycles are to be performed, the constant wear on the cutting edge eventually renders it incapable of cleanly severing a tissue sample.

Thus, the present invention contemplates forming the cutting board 31 of a material that reduces this frictional wear. In one embodiment, the cutting board 31 is formed of a material that is mechanically softer than the material of the cutting edge 35. However, the cutting board 31 cannot be so soft that the cutting edge 35 forms a pronounced circular groove in the cutting board, which significantly reduces the cutting efficiency of the inner cannula. In a most preferred embodiment of the invention, the cutting board 31 is formed of a plastic material, such as polycarbonate, ABS or DELRIN.RTM.

Returning again to FIGS. 1, 2 and 3A-3B, the rotary motor 20 includes a motor housing 39 that is sized to reciprocate within the handpiece 12. The housing 39 defines a pilot port 40 that is connected to the hydraulic control system 150 (see FIG. 10) by appropriate tubing. The present invention contemplates that the motor 20 can be a number of hydraulically powered rotating components. Most preferably, the motor 20 is an air motor driven by pressured air. Thus, the motor 20 includes a vaned rotor 42 that is mounted on a hollow tubular axle 43 extending through the motor housing 39. The axle 43 is supported on bearings 44 at opposite ends of the housing so that the rotor 42 freely rotates within the motor housing 39 under pneumatic pressure.

In the illustrated embodiment, tubular axle 43 is connected to the proximal end 37 of the inner cannula 17 by way of a coupler 46. The ends of the two tubes are mounted within the coupler 46 and held in place by corresponding set screws 47. Preferably the coupler 46 is formed of a plastic material that provides a generally airtight seal around the joint between the inner cannula 17 and the tubular axle 43. It is important that the coupler 46 provide a solid connection of the inner cannula 17 to the rotating components of the motor 20 so that the inner cannula 17 does not experience any torrential slip during the cutting operation.

Since the inner cannula 17 provides an avenue for aspiration of the biopsy sample, the invention further contemplates an aspiration tube 50 that mates with the tubular axle 43. Thus, the tissue aspiration path from the working end of the cutting element 11 is along the inner lumen 34 of the inner cannula 17, through the tubular axle 43 of the rotary motor 20, and through the aspiration tube 50 to a tissue collection location in the form of a collection trap 55. In order to maintain the vacuum or aspiration pressure within this aspiration path, the aspiration tube 50 must be fluidly sealed against the tubular axle 43. Thus, the motor housing 39 defines a mounting hub 51 into which the aspiration tube 50 is engaged. The position of the aspiration tube 50 is fixed by way of a setscrew 52 passing through the mounting hub 51. In contrast to the joint between the inner cannula 17 and the tubular axle 43, the joint between the aspiration tube 50 and the tubular axle 43 allows relative rotational between the two components. The tubular axle 43, of course, rotates with the rotor 42. However, the aspiration tube 50 need not rotate for use with the biopsy apparatus of the present invention. The mounting hub 51 can include an arrangement of seal rings (not shown) at the joint between the aspiration tube 50 and the tubular axle 43 to further seal the aspiration system.

The aspiration tube 50 communicates with a collection trap 55 that is removably mounted to the handpiece 12. The collection trap 55 includes a pilot port 107 that is connected by appropriate tubing to the hydraulic control system 150, as described in more detail herein. For the present purposes, it is understood that a vacuum or aspiration pressure is drawn through the pilot port 107 and the collection trap 55. This vacuum then draws a tissue sample excised at the working end of the cutting element 11, all the way through the inner cannula 17, tubular axle 43 and aspiration tube 50 until it is deposited within the trap. Details of the collection trap 55 will be discussed herein.

As explained above, the present invention contemplates an inner cannula 17 that performs its cutting operation by both rotary and reciprocating motion. Thus, the handpiece 12 supports a reciprocating motor 22. In one aspect of the invention, both motors 20 and 22 are hydraulically powered, most preferably pneumatically. This feature allows the motors to be formed of plastic, since no electrical components are required. In fact, with the exception of the outer cannula 15, trocar tip 16 and inner cannula 17, every component of the biopsy apparatus 10 in accordance with the present invention can be formed of a non-metallic material, most preferably a medical grade plastic. Thus, the biopsy apparatus 10 is eminently compatible with surgical imaging systems that may be used during the biopsy procedure. The compatibility of the apparatus 10 with Magnetic Resonance Imaging (MRI) is important because MRI is currently the only non-invasive visualization modality capable of defining the margins of the tumor. In addition, since the biopsy apparatus is formed of a relatively inexpensive plastic (as opposed to a more expensive metal), the entire apparatus can be disposable. Moreover, the elimination of substantially all metal components reduces the overall weight of the handpiece 12, making it very easily manipulated by the surgeon.

Referring most specifically to FIGS. 3A and 3B, the reciprocating motor 22 includes a pneumatic cylinder 60. The cylinder 60 includes a pilot port 61 that connects the cylinder to the hydraulic control system 150 through appropriate tubing. The motor 22 includes a piston 63 that reciprocates within the cylinder 60 in response to hydraulic fluid pressure provided at the pilot port 61. The piston 63 includes a central bore 64 for mounting the piston 63 to the aspiration tube 50. In one embodiment, the aspiration tube 50 is press-fit within the bore 64. The engagement between the aspiration tube 50 and the piston 63 can be enhanced by use of a set screw (not shown) or an adhesive or epoxy. At any rate, it is essential that the aspiration tube 50 and piston 63 move together, since the motor 22 must eventually drive the inner cannula 17 axially within the outer cannula.

It should be understood that in addition to powering the inner cannula, the piston 63 also reciprocates the rotary motor 20, which is essentially mounted to the reciprocating aspiration conduit. This movement is depicted by comparing the position of the rotary motor 20 between FIG. 3A and FIG. 3B. More specifically, the motor 20 as well as the aspiration conduit, including the inner cannula 17, moves within the handpiece 12. Preferably, the handpiece housing 70 is provided with openings 73 (FIG. 3B) at its opposite ends for slidably supporting the aspiration tube 50 and inner cannula 17. Since the distal housing 70 is preferably formed of a plastic material, no thrust bearings or rotary bearings are necessary to accommodate low friction axial movement of the cannula through the housing openings 73.

The biopsy apparatus 10 includes a handpiece 12 that carries all of the operating components and supports the outer and inner cannulas. The handpiece 12 includes a distal housing 70 within which is disposed the rotary motor 20. The distal end 71 of the housing 70 is configured into a fitting 72. This fitting 72 engages a mating flange 77 on an outer cannula hub 75. The hub 75 supports the outer cannula 15 within an engagement bore 76 (see FIG. 3B).

In accordance with one aspect of the invention, the engagement between the outer cannula hub 75 and the distal end 71 of the housing need not be airtight. In other words, the mating components of the fitting between the two parts need not be capable of generating a fluid-tight seal. In accordance with one embodiment of the invention, the engagement between the hub 75 and the housing 70 for supporting the outer cannula 15 provides a leak path 79 through the outer lumen 27 to the atmosphere. As be seen best in FIG. 3C, the leak path 79 extends between the housing 70 and the mating flange 77 of the outer cannula hub 75. In the use of the tissue biopsy apparatus 10, providing aspiration through the inner lumen 34 of the inner cutting cannula 17 will draw tissue through the inner lumen. As the tissue advances farther along the lumen, in some instances a vacuum can be created behind the advancing tissue. At some point in these instances, the tissue will stop advancing along the length of the inner lumen because the vacuum behind the tissue sample equals the vacuum in front of the tissue sample that is attempting to draw the sample to the collection trap 55. Thus, the leak path 79 through the outer lumen 27 allows atmospheric air to fall in behind the tissue sample when the inner cutter is retracted from the cutting board. The atmospheric air helps to relieve the vacuum behind the advancing tissue and aids in drawing the tissue down the length of the aspiration channel to the collection trap 55. However, in some applications, particularly where smaller "bites" of the target tissue are taken, the atomospheric air leak path 79 is not essential.

Preferably the fitting 72 and the mating flange 77 can be engaged by simple twisting motion, most preferably via Luer-type fittings. In use, the cannula hub 75 is mounted on the handpiece 12, thereby supporting the outer cannula 15. The handpiece can then be used to project the outer cannula into the body adjacent the sample site. In certain uses of the biopsy apparatus 10, it is desirable to remove the handpiece 12 from the cannula hub 75 leaving the outer cannula 15 within the patient. For example, the outer cannula 15 can be used to introduce an anesthetic. In other applications, once the target tissue has been completely excised, the outer cannula can be used to guide a radio-opaque marker to mark the location the removed material.

Returning again to the description of the housing 70, the housing defines an inner cavity 79 (best seen in FIG. 1) that is open through an access opening 81. The access opening 81 is preferably provided to facilitate assembly of the tissue biopsy apparatus 10. The distal end 71 of the housing 70 can be provided with a pair of braces 80 that add stiffness to the distal end 71 while the apparatus is in use. The braces 80 allow the distal end of housing 70 to be formed as a thin-walled plastic housing. Similar braces can be provided at the opposite end of the housing 70 as necessary to add stiffness to the housing.

The distal housing is configured to support the reciprocating motor 22 and in particular the cylinder 60. Thus, in one embodiment of the invention, the proximal end 83 of the distal housing 70 defines a pressure fitting 84. It is understood that this pressure fitting 84 provides a tight leak-proof engagement between the distal end 88 of the cylinder 60 and the proximal end 83 of the housing. In one specific embodiment, the pressure fitting 84 forms a spring cavity 85 within which a portion of the return spring 66 rests. In addition, in a specific embodiment, the pressure fitting 84 defines distal piston stop 86. The piston 63 contacts these stops at the end of its stroke. The location of the piston stop 86 is calibrated to allow the cutting edge 35 to contact the cutting board 31 at the working end of the cutting element 11 to allow the cutting edge to cleanly sever the biopsy tissue.

In the illustrated embodiment, the cylinder 60 is initially provided in the form of an open-ended cup. The open end, corresponding to distal end 88, fastens to the pressure fitting 84. In specific embodiments, the pressure fitting can include a threaded engagement, a press-fit or an adhesive arrangement.

The cylinder cup thus includes a closed proximal end 89. This proximal end defines the pilot port 61, as well as a central opening 62 (FIG. 3B) through which the aspiration tube 50 extends. Preferably, the proximal end 89 of the cylinder 60 is configured to provide a substantially airtight seal against the aspiration tube 50 even as it reciprocates within the cylinder due to movement of the piston 63. The proximal end 89 of the cylinder 60 defines a proximal piston stop 90, which can either be adjacent the outer cylinder walls or at the center portion of the proximal end. This proximal piston stop 90 limits the reverse travel of the piston 63 under action of the return spring 66 when pressure within the cylinder has been reduced.

In a further aspect of the invention, the collection trap 55 is mounted to the handpiece 12 by way of a support housing 93. It should be understood that in certain embodiments, the handpiece 12 can be limited to the previously described components. In this instance, the collection trap 55 can be situated separate and apart from the handpiece, preferably close to the source of vacuum or aspiration pressure. In this case, the proximal end of the aspiration tube 50 would be connected to the collection trap by a length of tubing. In the absence of the collection trap 55, the aspiration tube 50 would reciprocate away from and toward the proximal end of the cylinder 60, so that it is preferable that the handpiece includes a cover configured to conceals the reciprocating end of the aspiration tube.

However, in accordance with the most preferred embodiment, the collection trap 55 is removably mounted to the handpiece 12. A pair of longitudinally extending arms 94, that define an access opening 95 therebetween, forms the support housing 93. The support housing 93 includes a distal end fitting 96 that engages the proximal end 89 of cylinder 60. A variety of engagements are contemplated, preferably in which the connection between the two components is generally airtight. The proximal end 97 of the support housing 93 forms a cylindrical mounting hub 98. As best shown in FIG. 1, the mounting hub 98 surrounds a proximal end of the collection trap 55. The hub forms a bayonet-type mounting groove 99 that receives pins 103 attached to the housing 102 of the trap 55. A pair of diametrically opposite wings 104 can be provided on the housing 102 to facilitate the twisting motion needed to engage the bayonet mount between the collection trap 55 and the support housing 93. While the preferred embodiment contemplates a bayonet mount, other arrangements for removably connecting the collection trap 55 to the support housing 93 are contemplated. To be consistent with one of the features of the invention, it is preferable that this engagement mechanism be capable of being formed in plastic.

In order to accommodate the reciprocating aspiration tube, the support housing 93 is provided with an aspiration passageway 100 that spans between the proximal and distal ends of the housing. Since the aspiration tube 50 reciprocates, it preferably does not extend into the collection trap 55. As excised tissue is drawn into the trap 55, a reciprocating aspiration tube 50 can contact the biopsy material retained within the trap. This movement of the tube can force tissue into the end of the tube, clogging the tube. Moreover, the reciprocation of the aspiration tube can compress tissue into the end of the trap, thereby halting the aspiration function.

The collection trap 55 includes a housing 102, as previously explained. The housing forms a pilot port 107, which is connectable to a vacuum generator. Preferably in accordance with the present invention, appropriate tubing to the hydraulic control system 150 connects the pilot port 107. The trap 55 includes a filter element 110 mounted within the trap. In the preferred embodiment, the filter element is a mesh filter than allows ready passage of air, blood and other fluids, while retaining excised biopsy tissue samples, and even morcellized tissue. In addition, the filter element 110 is preferably constructed so that vacuum or aspiration pressure can be drawn not only at the bottom end of the filter element, but also circumferencially around at least a proximal portion of the element 110. In this way, even as material is drawn toward the proximal end of the filter, a vacuum can still be drawn through other portions of the filter, thereby maintaining the aspiration circuit.

Figure 4:
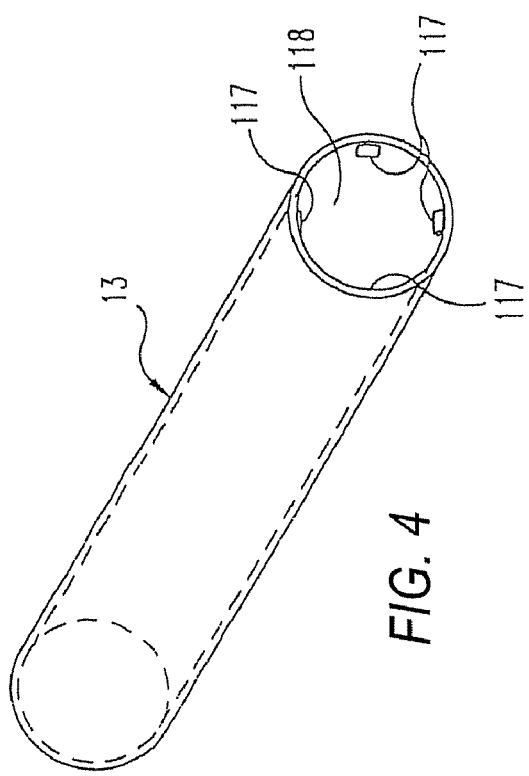
FIG. 4 is a perspective view of a cover for the tissue biopsy apparatus as shown FIG. 1.

The handpiece 12 can include individual covers for closing the access opening 81 in the distal housing 70 and the access openings 95 in the support housing 93. Those covers can support tubing for engagement with the pilot ports 40 and 61. Alternatively and most preferably, a single cover 13 as depicted in FIG. 4, is provided for completely enclosing the entire handpiece. The distal end 71 of the housing 70 can define a number of engagement notches 115 equally spaced around the perimeter of the distal end. The handpiece cover 13 can then include a like number of equally distributed tangs 117 projecting inwardly from the inner surface from the 118. These tangs are adapted to snap into the engagement notches 115 to hold the cover 113 in position over the handpiece 12. The cover can be attached by sliding axially over the handpiece 12. The cover 13 can include fittings for fluid engagement with the two pilot ports 40 and 61. Alternatively, the cover can be formed with openings for insertion of engagement tubing to mate with the respective pilot ports to provide hydraulic fluid to the rotary motor 20 and the reciprocating motor 22. In a specific embodiment, the cover 13 extends from the distal end 71 of the distal housing 70 to the proximal end 97 of the support housing 93. The cover can thus terminate short of the bayonet mounting feature between the support housing and the collection trap 55. Although not shown in the figures, the proximal end 97 of the support housing 93 can be configured to include a similar array of engagement notches with a corresponding array of mating tangs formed at the proximal end of the cover 13.

Figure 8:
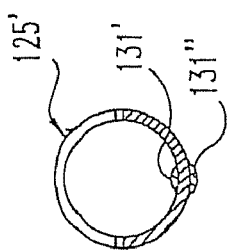
FIG. 8 is an end cross-sectional view similar to FIG. 7 showing a modified configuration for a stiffening member.
Figure 6:
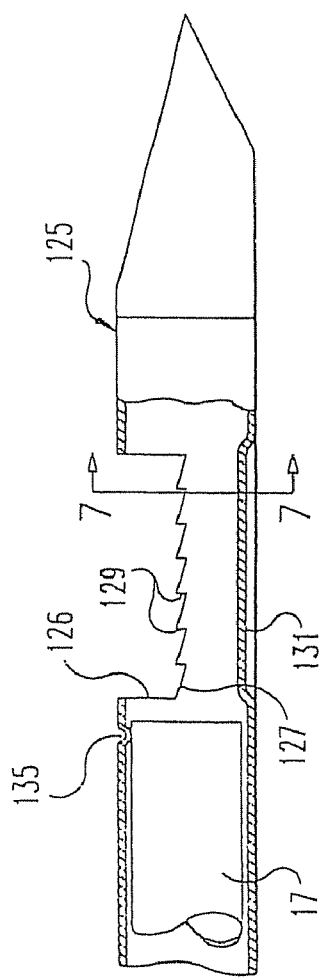
FIG. 6 is a side partial cross-sectional view of working end of a tissue biopsy apparatus in accordance with an alternative embodiment.
Figure 7:
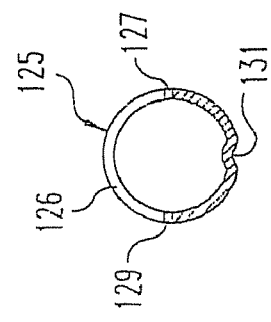
FIG. 7 is an end cross-sectional view of the apparatus depicted in FIG. 6, taken along lines 7-7 as viewed in the direction of the arrows.

Referring now to FIGS. 6-8, alternative embodiments of the outer cannula are depicted. As shown in FIG. 6 an outer cannula 125 includes a tissue-receiving opening 126. The opening is formed by opposite longitudinal edges 127. In one specific embodiment, a number of teeth 129 are formed at each longitudinal edge 127. As depicted in the figure, the teeth are proximally facing—i.e., away from the cutting board 31 (not shown) at the distal end of the outer cannula. With this orientation, the teeth 129 help prevent forward motion of tissue drawn into the opening 126 as the inner cannula 17 moves forward toward the cutting board. In prior devices, as the reciprocating cutting element advances through the outer cannula, the cutting edge not only starts to sever the tissue, it also pushes tissue in front of the inner cannula. Thus, with these prior devices, the ultimate length of the biopsy sample retrieved with the cut is smaller than the amount of tissue drawn into the tissue-receiving opening of the outer cannula. With the teeth 129 of the outer cannula 125 of this embodiment of the invention, the tissue sample removed through the inner cannula 17 is substantially the same length as the tissue-receiving opening 126. As the inner cannula 17 advances into the tissue, each of the teeth 129 tends to hold the tissue in place as the cutting edge 35 severs the tissue adjacent the outer cannula wall. With this feature, each "bite" is substantially as large as possible so that a large tissue mass can be removed with much fewer "bites" and in a shorter period of time. In addition to supporting the subject tissue as the inner cannula advances, the teeth can also cut into the tissue to prevent it from retracting out of the opening as the inner cutting cannula 17 advances.

The outer cannula 125 depicted in FIG. 6 can also incorporate a stiffening element 131 opposite the tissue-receiving opening 126. The stiffening element 131 adds bending stiffness to the outer cannula 125 at the distal end in order to maintain the longitudinal integrity of the outer cannula 125 as it is advanced into a tissue mass. In some prior devices that lack such a stiffening element, the working end of the cutting device is compromised as it bends slightly upward or downward as the outer cannula passes into the body. This bending can either close or expand the tissue-receiving opening, which leads to difficulties in excising and retrieving a tissue sample. The cutting mechanism of the present invention relies upon full, flush contact between the cutting edge of the inner cannula 17 and the cutting board 31. If the end of the outer cannula 125 is slightly askew, this contact cannot be maintained, resulting in an incomplete slice of the tissue sample.

Figure 8A:
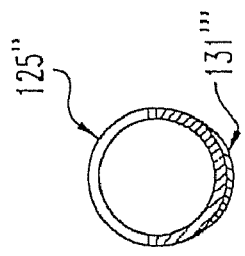
FIG. 8(a) is an end cross-sectional view similar to FIG. 7 showing a modified configuration for another stiffening member.

As depicted in the cross-sectional view of the FIG. 7, the stiffening element 131 in one embodiment is a crimp extending longitudinally in the outer wall of the cannula substantially coincident with the tissue-receiving opening 126. The outer cannula 125' depicted in FIG. 8 shows two additional versions of a stiffening element. In both cases, a bead of stiffening material is affixed to the outer cannula. Thus in one specific embodiment, a bead 131' is adhered to the inner wall of the outer cannula. In a second specific embodiment, a bead 131" is affixed to the outside of the outer cannula. In either case, the beads can be formed of a like material with the outer cannula, and in both cases, the beads provide the requisite additional bending stiffness. Another version of a stiffening element is shown if FIG. 8(a). In this case, a layer 131''' of additional stainless steel is bonded to the outer wall of the outer cannula 125".

Returning to FIG. 6, a further feature that can be integrated into the outer cannula 125 is the dimple 135. One problem frequently experienced by tube-within-a-tube cutters is that the inner reciprocating cutter blade contacts or catches on the outer cannula at the distal edge of the tissue-receiving opening. With the present invention, the dimple 135 urges the inner cannula 17 away from the tissue-receiving opening 126. In this way, the dimple prevents the cutting edge of the inner cannula 17 from catching on the outer cannula as it traverses the tissue-receiving opening. In the illustrated embodiment of FIG. 6, the dimple 135 is in the form of a slight crimp in the outer cannula 125. Alternatively, as with the different embodiments of the stiffening element, the dimple 135 can be formed by a protrusion affixed or adhered to the inner surface of the outer cannula. Preferably, the dimple 135 is situated immediately proximal to the tissue-receiving opening to help maintain the distance between the cutting edge and the tissue-receiving opening.

Figure 9:
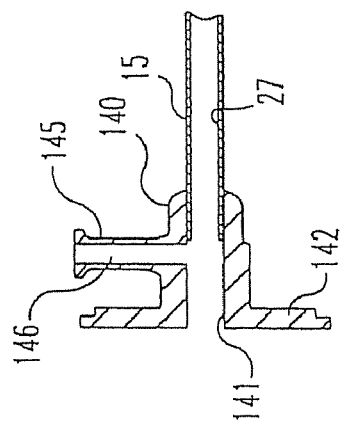
FIG. 9 is an enlarged side cross-sectional view of a fluid introduction port at the hub connecting the outer cannula to the handpiece for a tissue biopsy apparatus as depicted in FIG. 1.

As previously described, the outer cannula 15 is supported by a hub 75 mounted to the distal end of the handpiece. In an alternative embodiment depicted in FIG. 9, the outer cannula hub 140 provides a mean for introducing fluids into the outer lumen 27 of the outer cannula. Thus, the hub 140 includes an engagement bore 141 within which the outer cannula 15 is engaged. The hub also defines a flange 142 configured for mating with the fitting 72 at the distal end 71 of the housing 70. Thus, the outer cannula hub 140 is similar to the hub 75 described above. With this embodiment, however, an irrigation fitting 145 is provided. The fitting defines an irrigation lumen 146 that communicates with the engagement bore 141.

Ultimately, this irrigation lumen is in fluid communication with the outer lumen 27 of the outer cannula 15. The irrigation fitting 145 can be configured for engagement with a fluid-providing device, such as a syringe. The hub 140 thus provides a mechanism for introducing specific fluids to the biopsy site. In certain procedures, it may be necessary to introduce additional anesthetic to the sampling site, which can be readily accommodated by the irrigation fitting 145.

As discussed above, the preferred embodiment of the tissue biopsy apparatus 10 according to the present invention relies upon hydraulics or pneumatics for the cutting action. Specifically, the apparatus includes a hydraulic rotary motor 20 and a hydraulic reciprocating motor 22. While the apparatus 10 can be adapted for taking a single biopsy slice, the preferred use is to completely remove a tissue mass through successive cutting slices. In one typical procedure, the cutting element 11 is positioned directly beneath a tissue mass, while an imaging device is disposed above the mass. The imaging device, such as an ultra-sound imager, provides a real-time view of the tissue mass as the tissue biopsy apparatus 10 operates to successively remove slices of the mass. Tissue is continuously being drawn into the cutting element 11 by the aspiration pressure or vacuum drawn through the inner cannula 17. Successive reciprocation of the inner cannula 17 removes large slices of the mass until it is completely eliminated.

Figure 10:
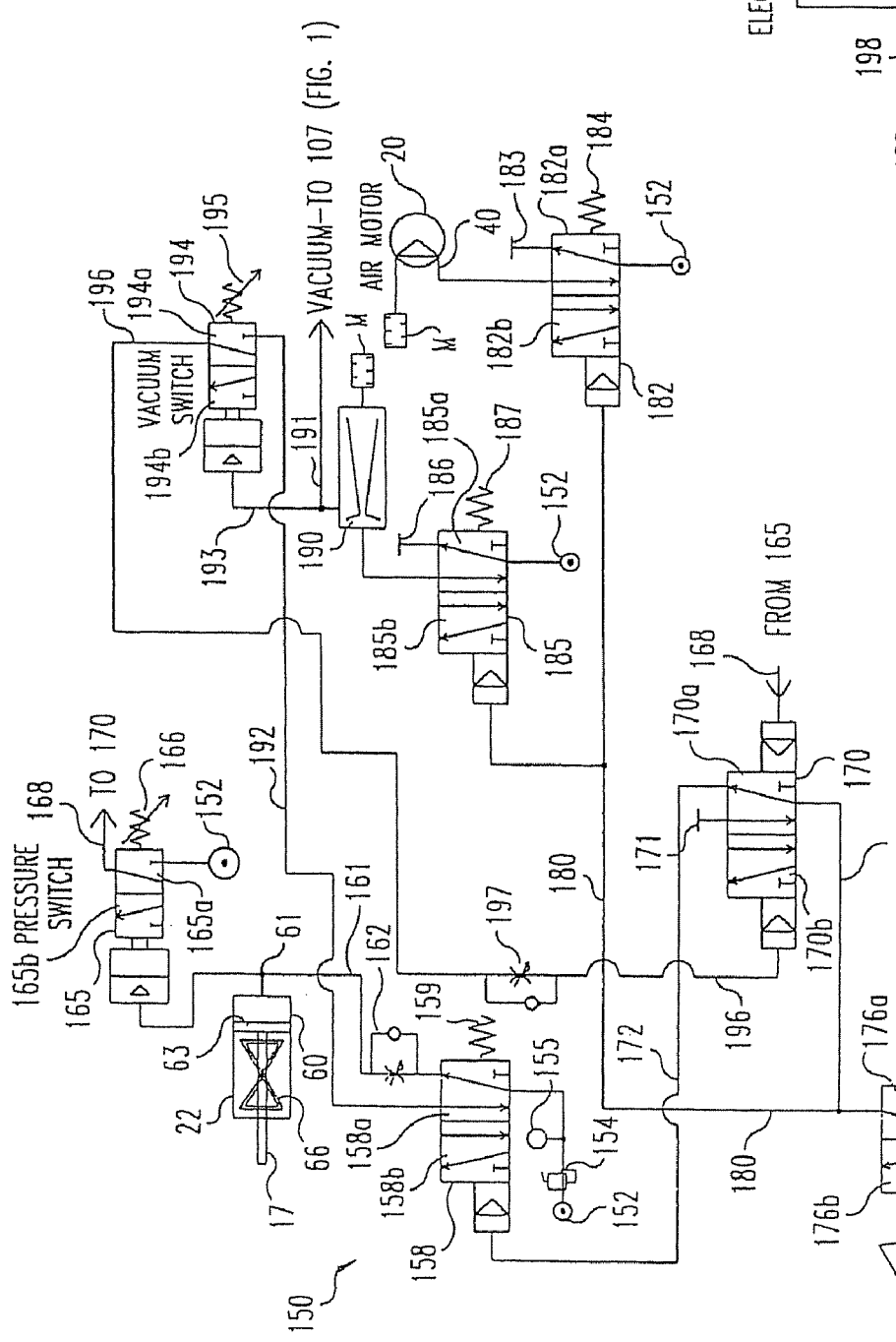
FIG. 10 is a schematic drawing of the hydraulic control system for the operation of the tissue biopsy apparatus shown in FIG. 1.

In order to achieve this continuous cutting feature, the present invention contemplates a hydraulic control system 150, as illustrated in the diagram of FIG. 10. Preferably the bulk of the control system is housed within a central console. The console is connected to a pressurized fluid source 152. Preferably the fluid source provides a regulated supply of filtered air to the control system 150.

As depicted in this diagram of FIG. 10, pressurized fluid from the source as provided at the several locations 152 throughout the control system. More specifically, pressurized fluid is provided to five valves that form the basis of the control system.

At the left center of the diagram of FIG. 10, pressurized fluid 152 passes through a pressure regulator 154 and gauge 155. The gauge 155 is preferably mounted on the console for viewing by the surgeon or medical technician. The pressure regulator 154 is manually adjustable to control the pressurized fluid provided from the source 152 to the two-position hydraulic valve 158. The valve 158 can be shifted between a flow path 158a and a flow path 158b. A return spring 159 biases the hydraulic valve to its normal position 158a.

In the normally biased position of flow path 158a, the valve 158 connects cylinder pressure line 161 to the fluid source 152. This pressure line 161 passes through an adjustable flow control valve 162 that can be used to adjust the fluid flow rate through the pressure line 161. Like the pressure gauge 155 and pressure regulator 154, the adjustable flow control valve 162 can be mounted on a console for manipulation during the surgical procedure.

The pressure line 161 is connected to the pilot port 61 of the reciprocating motor 22. Thus, in the normal or initial position of the hydraulic control system 150, fluid pressure is provided to the cylinder 60 to drive the piston 63 against the biasing force of the return spring 66. More specifically with reference to FIG. 3B, the initial position of the hydraulic valve 158 is such that the reciprocating motor and inner cannula are driven toward the distal end of the cutting element. In this configuration, the inner cannula 17 covers the tissue-receiving opening 25 of the outer cannula 15. With the inner cannula so positioned, the outer cannula can be introduced into the patient without risk of tissue filling the tissue-receiving opening 25 prematurely.

Pressurized fluid along cylinder pressure 161 is also fed to a pressure switch 165. The pressure switch has two positions providing flow paths 165a and 165b. In addition, an adjustable return spring 166 biases this switch to its normal position at which fluid from the pressure source 152 terminates within the valve. However, when pressurized fluid is provided through cylinder pressure line 161, the pressure switch 165 moves to its flow path 165b in which the fluid source 152 is hydraulically connected to the pressure input line 168. This pressure input line 168 feeds an oscillating hydraulic valve 170. It is this valve that principally operates to oscillate the reciprocating motor 22 by alternately pressurizing and releasing the two-position hydraulic valve 158. The pressure switch 165 is calibrated to sense an increase in pressure within the cylinder pressure line 161 or in the reciprocating motor cylinder 60 that occurs when the piston 66 has reached the end of its stroke. More specifically, the piston reaches the end of its stroke when the inner cannula 17 contacts the cutting board 31. At this point, the hydraulic pressure behind the piston increases, which increase is sensed by the pressure valve 165 to stroke the valve to the flow path 165b.

The oscillating hydraulic valve 170 has two positions providing flow paths 170a and 170b. In position 170a, input line 179 is fed to oscillating pressure output line 172. With flow path 170b, the input line 179 is fed to a blocked line 171. Thus, with fluid pressure provided from pressure switch 165 (through flow path 165b), the oscillating valve 170 opens flow path 170a which completes a fluid circuit along output line 172 to the input of the hydraulic valve 158.

Fluid pressure to output line 172 occurs only when there is fluid pressure within input line 179. This input line is fed by valve 176, which is operated by foot pedal 175. The valve 176 is biased by a return spring 177 to the initial position of flow path 176a. However, when the foot pedal 175 is depressed, the valve 176 is moved against the force of the spring to flow path 176b. In this position, pressurized fluid from the source 152 is connected to the foot pedal input line 179. When the oscillating hydraulic valve 170 is in its initial position flow path 170a, pressurized fluid then flows through input line 179 to output line 172 and ultimately to the hydraulic valve 158.

The fluid pressure in the output line 172 shifts the valve 158 to the flow path 158b. In this position, the fluid pressure behind the piston 63 is relieved so that the return spring 66 forces the piston toward the proximal end. More specifically, the return spring retracts the inner cannula 17 from the tissue cutting opening 25. The relief of the fluid pressure in line 161 also causes the pressure switch 165 to return to its initial neutral position of flow path 165a, due to the action of the return spring 166. In turn, with the flow path 165a, the pressure input line 168 is no longer connected to the fluid source 152, so no pressurized fluid is provided to the oscillating hydraulic valve 170. Since this valve is not spring biased to any particular state, its position does not necessarily change, except under conditions described herein.

Returning to the foot pedal 175 and valve 176, once the foot pedal is released, the biasing spring 177 forces the valve 176 from its flow path 176b to its normal initial flow path 176a. In this position the foot pedal input line 179 is no longer connected to the fluid source 152. When the oscillating valve 170 is at flow path 170a, the fluid pressure through output line 172 is eliminated. In response to this reduction in fluid pressure, hydraulic valve 158 is shifted to its original flow path 158a by operation of the return spring 159. In this position, the cylinder pressure line 161 is again connected to the fluid source 152, which causes the reciprocating motor 22 to extend the inner cannula 17 to its position blocking the tissue-receiving opening 25. Thus, in accordance with the present invention, the hydraulic control system 150 starts and finishes the tissue biopsy apparatus 10 with the tissue-receiving opening closed. It is important to have the opening closed once the procedure is complete so that no additional tissue may be trapped or pinched within the cutting element 11 as the apparatus is removed from the patient.

Thus far the portion of the hydraulic control system 150 that controls the operation of the reciprocating motor 22 has been described. The system 150 also controls the operation of the rotary motor 20. Again, in the most preferred embodiment, the motor 20 is an air motor. This air motor is controlled by another hydraulic valve 182. As shown in FIG. 10, the initial position of the valve provides a flow path 182a in which the fluid source 152 is connected to blocked line 183. However, when the hydraulic valve 182 is pressurized, it moves to flow path 182b in which the fluid source 152 is connected to the pilot port 140 of the air motor. In this position, pressurized fluid continuously drives the air motor 20, thereby rotating the inner cannula 17. It can be noted parathentically that a muffler M can be provided on the air motor to reduce noise.

The rotary motor hydraulic valve 182 is controlled by fluid pressure on pressure activation line 180. This activation line 180 branches from the foot pedal input line 179 and is connected to the foot pedal switch 176. When the foot pedal 175 is depressed, the switch moves to its flow path 176b. In this position the pressure activation line 180 is connected to the fluid source 152 so fluid pressure is provided directly to the rotary motor hydraulic valve 182. As with the other hydraulic valves, the valve 182 includes a biasing spring 184 that must be overcome by the fluid pressure at the input to the valve.

It should be understood that since the fluid control for the rotary motor 20 is not fed through the oscillating hydraulic valve 170, the motor operates continuously as long as the foot pedal 175 is depressed. In addition, it should also be apparent that the speed of the rotary motor 20 is not adjustable in the illustrated embodiment. Since the motor 20 is connected directly to the fluid source 152, which is preferably regulated at a fixed pressure, the air motor actually operates at one speed. On the other hand, as discussed above, the reciprocating motor 22 is supplied through a pressure regulator 154 and a flow control valve 162. Thus, the speed of reciprocation of the cutting blade 35 is subject to control by the surgeon or medical technician. The reciprocation of the cutting element 11 can be a function of the tissue being sampled, the size of the tissue biopsy sample to be taken, and other factors specific to the particular patient. These same factors generally do not affect the slicing characteristic of the cutting edge 35 achieved by rotating the inner cannula.

The hydraulic control system 150 also regulates the aspiration pressure or vacuum applied through the aspiration conduit, which includes the inner cannula 17. In the illustrated embodiment, the pressure activation line 180 branches to feed an aspiration valve 185. The valve is movable from its initial flow path 185a to a second flow path 185b. In the initial flow path, the fluid source 152 is connected to a blocked line 186. However, when fluid pressure is applied on line 180, the valve 185 shifts against the biasing spring 187 to the flow path 185b. In this path, the venturi element 190 is connected to the fluid source. This venturi element thus generates a vacuum in a vacuum control line 193 and in aspiration line 191. Again, as with the air motor, the venturi element 190 can include a muffler M to reduce noise within the handpiece.

As long as the foot pedal 175 is depressed and the valve 176 is in its flow path 176b, fluid pressure is continuously applied to the aspiration hydraulic valve 195 and the venturi element 190 generates a continuous vacuum or negative aspiration pressure. As with the operation of the rotary motor, this vacuum is not regulated in the most preferred embodiment. However, the vacuum pressure can be calibrated by a selection of an appropriate venturi component 190.

When the venturi component 190 is operating, the vacuum drawn on control line 193 operates on vacuum switch 194. A variable biasing spring 195 initially maintains the vacuum switch 194 at its flow path 194a. In this flow path, the vacuum input line 196 is not connected to any other line. However, at a predetermined vacuum in control line 193, the valve moves to flow path 194b. In this position, the vacuum input line 196 is connected to pressure line 192. In the preferred embodiment, the vacuum switch 194 operates in the form of a "go-nogo" switch—in other words, when the aspiration vacuum reaches a predetermined operating threshold, the vacuum switch is activated. When the vacuum switch 184 is initially activated, it remains activated as long as the foot pedal is depressed. Thus vacuum input line 196 is continuously connected to pressure line 192 as long as the foot pedal 175 is depressed.

Looking back to the hydraulic valve 158, the fluid pressure in line 192, and ultimately in vacuum input line 196, is determined by the state of valve 158. When the valve 158 is in its flow path 158a in which regulated fluid pressure is provided to the reciprocating motor 22, the pressure line 192 is dead. However, when the valve 158 moves to flow path 158b, pressure line 192 is connected to the regulated fluid source. Pressurized fluid then flows from pressure line 192, through vacuum switch flow path 194b, through vacuum input line 196 to the left side of oscillating valve 170, causing the valve to stroke to flow path 170b. When the oscillating valve 170 is in this flow path, output line 172 is dead, which allows valve 158 to move to its flow path 158a under the effect of the return spring 159. In this state, valve 158 allows pressurized fluid to again flow to the reciprocating motor 22 causing it to move through the next cutting stroke.

Thus, when both the valve 158 and the vacuum switch 194 are moved to their alternate states, pressurized fluid passes from line 192, through vacuum input line 196, and through an adjustable flow control valve 197 to a second input for the oscillating hydraulic valve 170. Pressure on the vacuum input line 196 shifts the oscillating valve 170 to its second position for flow path 170b. In this position, pressurized fluid passing through the foot pedal valve 176 terminates within valve 170. As a consequence, the pressure in output line 172 drops which allows the hydraulic valve 158 shift back to its original position 158a under operation of the return spring 159. In this position, fluid pressure is again supplied to the reciprocating motor 22 to cause the piston 66 to move through its cutting stroke.

It should be appreciated that the oscillating valve 170 is influenced by fluid pressure on lines 168 and 196, and that these lines will not be fully pressurized at the same time. When the system is initially energized, pressure from source 152 is automatically supplied to reciprocating motor 22 and pressure valve 165, causing the valve to move to flow path 165b. In this state, line 168 is pressurized which shifts oscillating valve 170 to the left to state 170*a*. The oscillating valve will remain in that state until line 196 is pressurized, regardless of the position of pressure switch 165. It can also be appreciated that in the preferred embodiment, the fluid pressure on line 196 does not increase to operating levels until the foot pedal 175 has been depressed and the aspiration circuit has reached its operating vacuum.

In an alternative embodiment, the vacuum switch 194 can be calibrated to sense fine changes in vacuum. In this alternative embodiment, the completion of this return stroke can be determined by the state of the vacuum switch 194. The vacuum switch 194 can operate as an indicator that a tissue sample has been drawn completely through the aspiration conduit into the collection trap 55. More specifically, when the vacuum sensed by vacuum switch 194 has one value when the inner cannula is open to atmospheric pressure. This vacuum pressure changes when a tissue sample is drawn into the inner cannula 17. The vacuum pressure changes again when the tissue is dislodged so that the inner cannula is again open to atmospheric pressure. At this point, the inner cannula 17 is clear and free to resume a cutting stroke to excise another tissue sample. Thus, the vacuum switch 194 can stroke to its flow path 194*b* to provide fluid pressure to the left side of the oscillating valve 170, causing the valve to stroke to flow path 170*b*.

It can be appreciated from this detail explanation that the hydraulic control system 150 provides a complete system for continuously reciprocating the axial motor 22. In addition, the system provides constant continuous pressure to both the rotary motor 20 and the aspiration line 191, so long as the foot pedal 175 is depressed. Once the foot pedal is released, fluid pressure in activation line 180 drops which causes the air motor control valve 182 and the aspiration control valve 185 to shift to their original or normal positions in which fluid pressure is terminated to those respective components. However, in the preferred embodiment, pressure is maintained to the reciprocating motor 22 because the motor is fed through valve 158, which is connected directly to the fluid source 152.

The hydraulic control system 150 in the illustrated embodiment incorporates five controllable elements. First, the fluid pressure provided to activate the reciprocating motor 22 is controlled through the regulator 154. In addition, the fluid flow rate to the piston 66 is controlled via the adjustable control valve 162. The pressure at which the pressure switch 165 is activated is determined by an adjustable return spring 166. Likewise, the aspiration pressure vacuum at which the vacuum switch 194 is activated is controlled by an adjustable return spring 195. Finally the adjustable flow control valve 197 controls the fluid flow from the vacuum switch 194 to the oscillating hydraulic valve 170. Each of these adjustable elements controls the rate and duration of oscillation of the reciprocating motor 22.

In the preferred embodiment, the pressure switch 165 essentially operates as an "end of stroke" indicators. In other words, when the inner cannula 17 reaches the end of its forward or cutting stroke, it contacts the cutting board 31. When it contacts the cutting board, the pressure in the cylinder pressure line 161 changes dramatically. It is this change that causes the pressure switch 165 to change states. This state change causes the oscillating valve 170 to shift valve 158 to terminate fluid pressure to the motor 22, causing it to stop its cutting stroke and commence its return stroke.

During this return stroke, the excised tissue sample is gradually drawn along the aspiration conduit. Also during the return stroke, fluid pressure bleeds from pressure line 161 and pressure switch 165 and ultimately from line 168 feeding oscillating valve 170. When this valve strokes, fluid pressure bleeds from valve 158 allowing the valve to return to state 158*a* to pressurize the motor 22 for a new cutting stroke. The operation of each of these hydraulic valves introduces an inherent time delay so that by the time the pressure to the reciprocating motor 22 has been restored the aspiration vacuum has pulled the tissue sample through the entire aspiration conduit and into the collection trap 55.

The use of a hydraulically controlled inner cutting cannula provides significant advantages over prior tissue cutting devices. The use of hydraulics allows most of the operating components to be formed of inexpensive and light-weight non-metallic materials, such as medical-grade plastics. The hydraulic system of the present invention eliminates the need for electrical components, which means that electrical insulation is unnecessary to protect the patient.

Perhaps most significantly, the hydraulically controlled reciprocation of the inner cutting cannula provides a cleaner and better-controlled cut of biopsy tissue. Since the reciprocating motor 22 is fed from a substantially constant source of pressurized fluid, the pressure behind the motor piston 63 remains substantially constant throughout the cutting stroke. This substantially constant pressure allows the inner cutting cannula to advance through the biopsy tissue at a rate determined by the tissue itself.

In other words, when the cutting edge 35 encounters harder tissue during a cutting stroke, the rate of advancement of the motor piston 63 and therefor the inner cannula 17 decreases proportionately. This feature allows the cutting edge to slice cleanly through the tissue without the risk of simply pushing the tissue. The rotation of the cutting edge can facilitate this slicing action. When the inner cannula encounters less dense tissue, the constant pressure behind the piston 63 allows the cutting edge to advance more quickly through the tissue.

Figure 11:
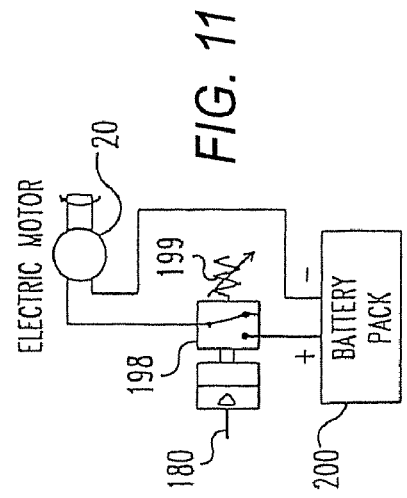
FIG. 11 is a schematic drawing of an electric motor control system according to another embodiment.

In alternative embodiment, the rotary motor 20 can consist of an electric motor, rather than a pneumatic motor. As depicted in FIG. 11, the pressure activation line 180 can be fed to an on-off pressure switch 198 that is governed by an adjustable bias spring 199. When the activation line 180 is pressurized the switch 198 establishes a connection between an electric reciprocating motor 20 and a battery pack 200. Preferably, the battery pack 200 is mounted within the handpiece 12, but can instead be wired to an external battery contained within the console.

In the preferred embodiment, the tissue biopsy apparatus 10 depicted in FIG. 1 has an overall length of under sixteen inches (16") and an outer diameter less than one and one quarter inches (1.25"). The outer cannula and therefore the cutting element 11 have a length measured from the handpiece 12 of approximately five inches (5"). The outer cannula preferably has a nominal outer diameter of 0.148" and a nominal inner diameter of 0.136". The inner cannula most preferably has a nominal outer diameter of 0.126" so that it can reciprocate freely within the outer cannula without catching on the tissue cutting opening. The inner cannula has a nominal wall thickness of 0.010", which yields a nominal inner lumen diameter of about 0.106."

The length of the tissue-receiving opening determines the length of biopsy sample extracted per each oscillation of the reciprocating motor 22. In one specific embodiment, the opening has a length of about 0.7", which means that a 0.7" long tissue sample can be extracted with each cutting cycle. In order to accommodate a large number of these biopsy tissue slugs, the collection trap can have a length of about 2.5" and a diameter of about 0.05". Of course, the interior volume of the collection trap can vary depending upon the size of each biopsy slug and the amount of material to be collected. In a specific embodiment, the filter disposed within the collection trap 55 manufactured by Performance Systematix, Inc. of Callondoni, Mich.

In accordance with a specific embodiment, the cutting stroke for the inner cannula is about 0.905". The return spring 66 within the reciprocating motor 22 is preferably a conical spring to reduce the compressed height of the spring, thereby allow a reduction in the overall length of the hydraulic cylinder 60. In addition, the return spring 66 can be calibrated so that the return stroke occurs in less than about 0.3 seconds. Preferably, the inwardly beveled surface 36 of cutting edge 35 is oriented at an approximately 30.degree. angle.

The aspiration pressure vacuum is nominally set at 27 in.Hg. during the cutting stroke. When the cannula is retracted and the outer lumen 27 is open, the vacuum pressure is reduced to 25 in.Hg. This aspiration pressure normally allows aspiration of a tissue sample in less than about 1 second and in most cases in about 0.3 second. In accordance with a most preferred embodiment, the hydraulic control system 150 preferably is calibrated so that the inner cannula dwells at its retracted position for about 0.3 seconds to allow complete aspiration of the tissue sample. Adjusting the return spring 195 of the vacuum switch 194 can control this dwell rate.

In a preferred embodiment, the inner cannula 17 can advance through the cutting stroke in about two seconds. This stroke speed can be accomplished with a regulated pressure at source 152 of about 20 p.s.i. When the inner cannula reaches the end of its cutting stroke, the pressure can increase at about five p.s.i. per second. Preferably, the return spring 166 of the pressure switch 165 is set so that the end of cutting stroke is sensed within about 0.5 seconds.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

EXAMPLES

Example 1

Eighteen trial biopsies were performed upon patients after obtaining informed consent and preparing the patients according to standard biopsy procedures. In each case, biopsies were performed according to the following procedure. The patient was positioned on her back on the surgical table, and the lesion was located using ultrasound. A small incision was made in the breast. While viewing the lesion using ultrasound, an early embodiment of the present invention was inserted into the breast with the tissue receiving opening adjacent the lesion. The cutter was engaged to sample and/or remove the lesion. The lesions varied in size from 6-22 mm. The surgeon's comments are provided in Table 1. TABLE-US-00001 TABLE 1 Surgeon's Comments Regarding the Use of Early Embodiments of the Present Biopsy Device Trial Number Surgeon's Comments 1 Went very well, lesion took approximately 50 seconds to go away 2 Large fatty breast, very difficult to get needle to mass; eventually successfully removed 3 Successfully removed without problems 4 Went very well; lesion gone in 4-5 cores 5 Two lesions attempted (1) lesion easily removed, (2) inner cutter was riding up and catching the opening 6 Only took 4-5 cores to disappear 7 Started getting good cores, then stopped cutting due to secondary electrical break 8 Lesion appeared to be totally gone, cores were up to 25 mm in length 9 Only got 4-5 good cores, then stopped cutting due to inner cutter riding up 10 No problems 11 No problems at all 12 Lesion was easily palpable but very mobile which made access difficult. Used tactile sensation to manipulate tumor into aperture which worked very well; very good cores; Took 4.5 minutes but many of the cores were fatty as a lot of the time I was missing the lesion before realizing that palpitation was better 13 Took 3-4 cores then quit cutting, blade was dulled, probably due to deflection of tip downward 14 Went very well, no problems 15 Went well, no problems 16 Went well, no problems 17 Went very well 18 Went very well, the suction tubing collapsed, need stronger tubing; filter did fill up requiring stopping to empty, might need larger filter.

Table 1 illustrates the success of the present invention in its early stage of development. A majority of the trials, trials 1-6, 8, 1-12, and 14-18, resulted in a successful removal of the lesion with little to no problems. Lesions were removed quickly and, in some cases, only a few cores were required (see trials 1, 4, and 6). In trial number 8 it was noted that the cores were up to 25 mm in length.

In some trials, the surgeon experienced difficulties removing the lesion because the inner cutting blade would ride up and catch on the tissue receiving opening (see trials 5, and 9). However, this problem has been resolved in the present invention by integrating a crimp in the outer cannula. The crimp forms a dimple that protrudes from the inner surface of the cannula and into the outer lumen. As the inner cannula passes the dimple, the dimple forces the inner cannula away from the tissue-receiving opening and prevents the inner cannula from riding up into the opening. In a further embodiment, the cutting edge of the inner cannula is inwardly beveled. This inwardly beveled surface also helps eliminate risk of catching by guiding the inner cannula back into the hollow outer cannula. In addition, to prevent the deflection of the tip downward, as noted in trial 13, a stiffening element is provided on the outer cannula opposite the tissue-receiving opening.

Example 2

Surgeons performing biopsies using the device of this invention and a device having the features of U.S. Pat. No. 5,526,822 to Burbank provided feedback as to the efficiency of each device. The surgeons' input was used to calculate the amount of time and the number of strokes necessary to remove a lesion. Table 2 compares the amount of time and the number of strokes necessary to remove comparable lesions using each device. TABLE-US-00002 TABLE 2 Comparison of Removal Times and Number of Strokes of the Present Biopsy Device with the Prior Art Device Present Biopsy Device Prior Art Removal Times (sec) Lesion Diameter 10 80 500 13 135 845 16 205 1280 No. of Strokes Lesion Diameter 10 16 25 13 27 42 16 41 64.

This data demonstrates that the present tissue biopsy apparatus consistently removes a lesion with fewer strokes and in less time than the prior cutter. The present tissue biopsy device performs 80% faster than the prior cutter, which ultimately results in reduced trauma to the tissue.

CONCLUSION

The biopsy devices of this invention reliably, quickly and efficiently sample and remove lesions in tissue.

What is claimed is:

1. A method of relieving vacuum in a biopsy apparatus that comprises a first cannula defining a first lumen therethrough and a tissue-receiving opening in communication with the first lumen; a second cannula slidably disposed in the first lumen, wherein the second cannula defines a second lumen therethrough, and a vacuum source in fluid communication with the second lumen, the method comprising:

applying vacuum from the vacuum source through at least one motor to the second lumen;

providing an open leak path through an engagement area between a first cannula mounting hub and a housing that permits fluid communication between the first lumen and the atmosphere, the leak path is continuously open and fluid is drawn from the leak path and through the first cannula;

retracting the second cannula to permit tissue to prolapse into the tissue receiving opening due to the vacuum created through the second lumen;

translating the second cannula toward the distal end of the first cannula to sever the tissue that has prolapsed into the tissue receiving opening;

aspirating the severed tissue through the second lumen; and selectively relieving vacuum distally of the severed and aspirating tissue by retracting the second cannula away from the distal end of the first cannula thereby permitting the second lumen to communicate with the first lumen and the leak path while a portion of the biopsy apparatus, including the tissue receiving opening, is positioned within tissue.

2. The method of claim 1, wherein the vacuum is applied continuously.

3. The method of claim 1, wherein the second cannula is at least one of (i) rotated within the first cannula and (ii) reciprocated within the first cannula, to sever the tissue that has prolapsed into the tissue receiving opening.

4. The method of claim 3, wherein the second cannula is rotated simultaneously when the second cannula is translated.

5. The method of claim 1, wherein a distal end of the second cannula is spaced inwardly from a proximal edge of the tissue receiving opening of the first cannula, prior to the second cannula being translated distally toward the distal end of the first cannula to cut tissue.

6. The method of claim 1, wherein the fluid that that is drawn from the leak path is air.

7. A method of controlling a biopsy device to clear a tissue sample disposed within the biopsy device, the biopsy device comprising a continuously open leak path, an inner cannula and an outer cannula, the outer cannula having a outer lumen, a distal end and a tissue receiving opening proximal to the distal end, the inner cannula having an inner lumen and being disposed coaxially and slidably relative to the outer cannula, the leak path being in fluid communication the outer lumen and a fluid source, the method comprising:

applying vacuum from a vacuum source though the inner lumen;

retracting the inner cannula from a position distal to a distal edge of the tissue receiving opening to a position proximal to the distal edge of the tissue receiving opening;

drawing a fluid into the biopsy device through the leak path to relieve a vacuum formed distal of the tissue sample.

8. The method of claim 7, wherein the fluid source is atmospheric air.

* * * * *